United States Patent
Teramura et al.

(10) Patent No.: US 10,047,353 B2
(45) Date of Patent: Aug. 14, 2018

(54) GRIMONITIA-HOLLISAE-DERIVED RECOMBINANT COLLAGENASE AND ENZYME AGENT FOR CELL AND TISSUE DISSOCIATION

(71) Applicants: Nippi, Incorporated, Tokyo (JP); The University of Tokyo, Tokyo (JP)

(72) Inventors: Naoko Teramura, Tokyo (JP); Katsumasa Iijima, Tokyo (JP); Osamu Hayashida, Tokyo (JP); Keisuke Tanaka, Tokyo (JP); Shunji Hattori, Tokyo (JP); Teru Okitsu, Tokyo (JP); Shoji Takeuchi, Tokyo (JP)

(73) Assignees: Nippi, Incorporated, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 15/123,986

(22) PCT Filed: Mar. 6, 2015

(86) PCT No.: PCT/JP2015/056748
§ 371 (c)(1),
(2) Date: Sep. 6, 2016

(87) PCT Pub. No.: WO2015/133636
PCT Pub. Date: Sep. 11, 2015

(65) Prior Publication Data
US 2017/0218352 A1    Aug. 3, 2017

(30) Foreign Application Priority Data

Mar. 6, 2014 (JP) .................................. 2014-044205

(51) Int. Cl.
*C12N 9/52* (2006.01)

(52) U.S. Cl.
CPC ........ *C12N 9/52* (2013.01); *C12Y 304/24007* (2013.01)

(58) Field of Classification Search
None
See application file for complete search history.

(56) References Cited

U.S. PATENT DOCUMENTS

2010/0159564 A1    6/2010    Dwulet et al.

FOREIGN PATENT DOCUMENTS

| EP | 0430635 A1 | 6/1991 |
| JP | 08-070853 | 3/1996 |
| JP | 2010-263880 | 11/2010 |
| JP | 2011-024439 | 2/2011 |
| WO | 1998/022574 A2 | 5/1998 |

OTHER PUBLICATIONS

Accession AYL91549. Jan. 20, 2011.*
Chica et al. Curr Opin Biotechnol. Aug. 2005;16(4):378-84.*
Singh et al. Curr Protein Pept Sci. 2017, 18, 1-11.*
Accession F7IZI6. Sep. 21, 2011.*
Ijima, et al. "0-53 Development of novel recombinant collagenase formulation derived from Grimontia hollisae for clinical isolation" 41st Annual Congress of Japanese Pancreas Shorokushu, Feb. 2014, p. 101.
Ohbayashi, et al. "Analysis of intramolecular conformational changes of multidomain protein collagenases", Journal of Japanese Biochemical Society or SEIKAGAKU, vol. 85, No. 8, pp. 692-699, 2013.
Koki Suzuki "Properties of collagenase preparated from the culture of Vibrio hollisae 1706B strain", Hikaku Kagaku, 2000, vol. 45, No. 4, pp. 272-283.
Teramura, et al. "Cloning of a Novel Collagenase Gene from the Gram-Negative Bacterium Grimontia (Vibrio) hollisae 1706B and Its Effecient Expression in Brevibacillus Choshinensis", Journal of Bacteriology, Jun. 2011, vol. 193, No. 12, p. 3049-3056.
Yeats et al., New knowledge from old: In silico discovery of novel protein domains in *Streptomyces coelicolor*. BMC Microbiology, vol. 3, No. 1, pp. 1-20 (2003).
Extended European Search Report dated Aug. 17, 2017 for European Application Serial No. 15757886.

* cited by examiner

*Primary Examiner* — Christian Fronda
(74) *Attorney, Agent, or Firm* — K&L Gates LLP; Louis C. Cullman; David Diamond

(57) ABSTRACT

Recombinant collagenases with a stable specific activity and enzyme agents for cell and tissue dissociation such a recombinant are provided. The recombinant collagenase is derived from *Grimontia hollisae*-derived collagenase is characterized by having, from the N terminus to the C terminus, a collagenase catalytic domain, a linker region sequence, and a prepeptidase C terminal domain, which *Grimontia hollisae*-derived recombinant collagenase does not comprise at least the prepeptidase C terminal domain. The obtained recombinant collagenase has a high and stable specific activity.

4 Claims, 12 Drawing Sheets

Photograph of the pancreatic islets
under an optical microscope

Fig.8
A
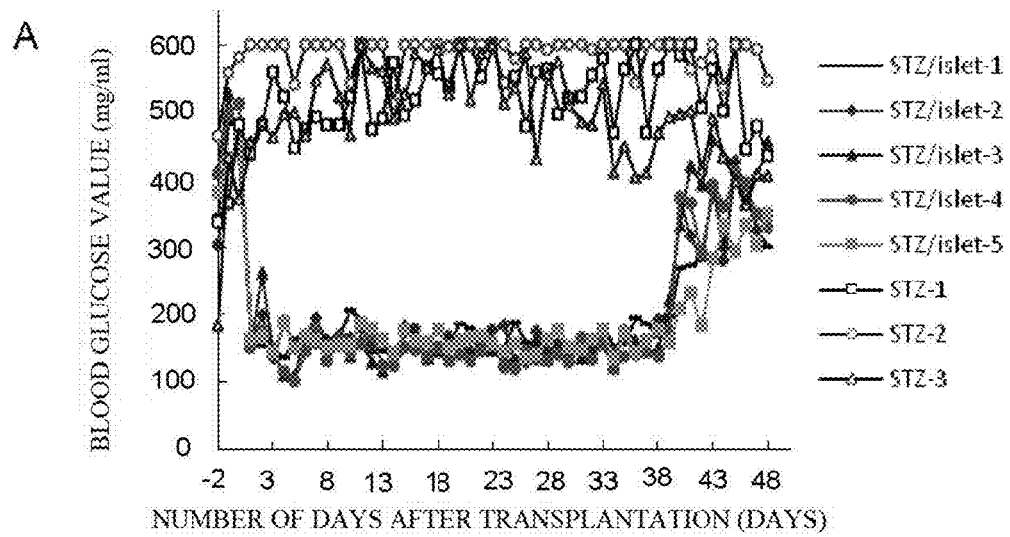
B
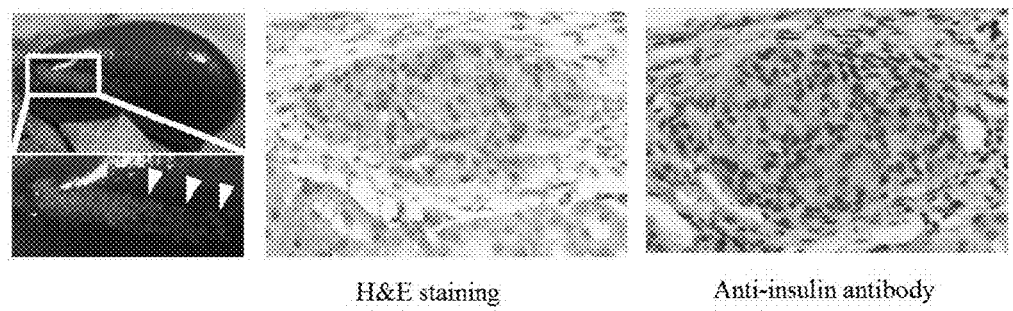
H&E staining　　　Anti-insulin antibody

Photograph of liver cells under phase-contrast microscopy

SEQUENCE LISTING

```
<160> NUMBER OF SEQ ID NOS: 15

<210> SEQ ID NO 1
<211> LENGTH: 767
<212> TYPE: PRT
<213> ORGANISM: Grimontia hollisae

<400> SEQUENCE: 1

Met Glu Leu Lys Ala Leu Ala Leu Thr Val Ser Ala Leu Leu Val Gly
1               5                   10                  15

Gln Ser Val Tyr Ala Ser Glu Val Phe Ala His Pro Gly Met Pro Val
            20                  25                  30

Gln Gln Lys Leu Gln Pro Asn Leu Leu Gln Gln Ser Thr Arg Leu Gln
        35                  40                  45

Pro Glu Gln His Ile His Gly Leu Glu Arg Thr Asp Arg Gln Tyr Arg
    50                  55                  60

Pro Thr Asp Ala Thr Gln Gln Pro Glu Pro Pro Thr Leu Leu Lys Arg
65                  70                  75                  80

Gln Val Ser Val Gln Gln Asp Ala Val Glu Gln Cys Asp Leu Ser Gln
                85                  90                  95

Phe Gln Thr Thr Ser Ser Asn Gln Leu Met Ala Ala Ile Arg Gln Gln
            100                 105                 110

Gly Ala Ser Cys Val Asn Ala Leu Phe Ser Ala Asp Thr Gly Val Gln
        115                 120                 125

Glu Ala Ala Phe Ser Ser Asn His Met Tyr Asn Val Ala Gln Tyr Thr
    130                 135                 140

Arg Thr Leu Ala Gln Gln Tyr Ala Gly Gly Ser Asp Glu Leu Glu
145                 150                 155                 160

Ala Leu Tyr Leu Tyr Leu Arg Ala Gly Tyr Tyr Ala Glu Phe Tyr Asn
                165                 170                 175

Ser Asn Ile Thr Phe Leu Ser Trp Val Thr Pro Ala Val Lys Gly Ala
            180                 185                 190

Val Asp Ala Phe Val Gln Asn Ala His Phe Tyr Asp Asn Gly Asp Ala
        195                 200                 205

His Gly Lys Val Leu Asn Glu Val Ile Ile Thr Met Asp Ser Ala Gly
    210                 215                 220

Leu Gln His Ala Tyr Leu Asp Val Val Thr Gln Trp Leu Thr Arg Trp
225                 230                 235                 240

Asn Ala Gln Tyr Ala Glu His Trp Tyr Met Arg Asn Ala Val Asn Gly
                245                 250                 255
```

```
Val Phe Thr Leu Leu Phe Gly Gly Gln Trp Asn Asn Gln Tyr Thr Ser
            260                 265                 270

Leu Ile Gly Glu Gln Thr Ala Leu Val Thr Ala Leu Gln Ala Phe Ala
        275                 280                 285

Leu Asp Arg Thr Lys Val Asn Ser Pro Thr Glu Phe Met Ala Ala Asn
    290                 295                 300

Ala Ala Arg Glu Leu Gly Arg Leu Ala Arg Tyr Thr Asp Ala Thr Ile
305                 310                 315                 320

Ala Pro Lys Val Thr Glu Gly Leu Thr Ala Ile Phe Gly Gln Tyr Pro
                325                 330                 335

Ser Tyr Gly Asp Gly Asp Ala Ile Trp Leu Gly Ala Ala Asp Thr Ala
            340                 345                 350

Ser Tyr Tyr Ala Asp Cys Ser Gln Phe Asn Ile Cys Gly Phe Glu Asp
        355                 360                 365

Ala Leu Arg Asp Ala Ala Leu Asn Gln Thr Phe Ile Cys Ser Asp Thr
    370                 375                 380

Ile Lys Ile Arg Ser Gln Asp Met Ser Gln Ala Gln His Leu Ala Ala
385                 390                 395                 400

Cys Asp Lys Met Ala Tyr Glu Glu Ser Phe Phe His Thr Thr Leu Glu
                405                 410                 415

Thr Gly Asn Gln Pro Val Ala Asp Asp His Asn Thr Gln Leu Gln Val
            420                 425                 430

Asn Ile Phe Asn Ser Asp Thr Asp Tyr Gly Lys Tyr Ala Gly Pro Ile
        435                 440                 445

Phe Gly Ile Asp Thr Asn Asn Gly Gly Met Tyr Leu Glu Gly Asn Pro
    450                 455                 460

Ala Asn Val Gly Asn Ile Pro Asn Phe Ile Ala Tyr Glu Ala Ser Tyr
465                 470                 475                 480

Ala Asn Pro Asp His Phe Val Trp Asn Leu Glu His Glu Tyr Val His
                485                 490                 495

Tyr Leu Asp Gly Arg Phe Asn Met Tyr Gly Asp Phe Gly Thr Pro Thr
            500                 505                 510

Glu Leu Val Val Trp Trp Ser Glu Gly Val Ala Glu Tyr Val Ser Arg
        515                 520                 525

Val Asn Asp Asn Pro Gln Ala Ile Ala Thr Ile Gln Asp Gly Ser Thr
    530                 535                 540

Tyr Thr Leu Ala Gln Val Phe Asp Thr Thr Tyr Asp Gly Phe Asp Val
545                 550                 555                 560

Asp Arg Ile Tyr Arg Trp Gly Tyr Leu Ala Val Arg Phe Met Phe Glu
                565                 570                 575

Arg His Pro Asp Glu Val Gln Arg Met Leu Ser Ala Thr Arg Gln Gly
            580                 585                 590

Arg Trp Ala Glu Tyr Lys Ala Ile Ile Ser Gly Trp Ala Asn Gln Tyr
        595                 600                 605

Gln Ser Glu Phe Ala Gln Trp Thr Glu Ala Leu Ala Lys Gly Asp Ser
    610                 615                 620

Gly Ala Gly Asn Gly Glu Gly Thr Gly Ser Gly Asn Glu Gly Gly Gly
625                 630                 635                 640

Glu Ser Gly Gly Asn Thr Gly Leu Pro Glu Asn Cys Ala Val Leu Pro
                645                 650                 655

Lys Ile Ser Asp Gly Arg Leu Ala Leu Asp Glu Ala Ala Cys Leu Ala
            660                 665                 670

Asp Thr Ala Ser Ala Ser Asp Val Leu Trp Phe Ser Ile Pro Ala Val
```

```
                675                 680                 685
Ser Glu Tyr Gln Thr Ile Ala Ile Thr Ala Gly Asn Gly Thr Gly Asp
            690                 695                 700

Leu Thr Leu Glu Tyr Ser Asn Leu Asn Trp Pro Asp Gly Thr Asn Val
705                 710                 715                 720

Gln Ala Ser Ser Ala Asn Met Gly Asn Ser Glu Cys Ile Ile Leu Glu
            725                 730                 735

His Gln Ala Asn Tyr Trp Gly Tyr Leu Lys Val Ser Gly Ser Phe Glu
            740                 745                 750

Asn Ala Ala Leu Leu Val Glu Ala Gly Ser Asn Gln Cys Arg Gln
            755                 760                 765

<210> SEQ ID NO 2
<211> LENGTH: 2304
<212> TYPE: DNA
<213> ORGANISM: Grimontia hollisae

<400> SEQUENCE: 2
```

| | | | | |
|---|---|---|---|---|
| atggaactta aagcacttgc gttaacggta tcagccctgc ttgtgggtca gtcggtgtat | 60 |
| gcatctgagg tgtttgctca cccgggcatg ccggttcaac aaaagttgca gccaaatttg | 120 |
| ctgcagcaaa gtaccaggct tcagccagag caacatatcc acgggcttga cgcacggat | 180 |
| cggcaatatc gtccgacaga tgctactcag cagccggaac cgccaacgtt actgaaacgt | 240 |
| caggtatcgg ttcagcagga tgcggttgaa cagtgtgatc tcagccagtt tcagacgacc | 300 |
| agcagtaacc agttgatggc cgcgattcgc cagcagggcg ccagttgtgt caatgccttg | 360 |
| tttagtgctg acacgggagt acaggaagcc gcgttttcgt ccaaccacat gtataacgtc | 420 |
| gcacaatata cccgaacact ggcgcagcaa tatgcgggcg ggggcagtga tgaactggaa | 480 |
| gccttatatc tgtatcttcg gcggggtat tacgctgagt tttataacag caatatcacg | 540 |
| tttctgtcgt gggtgacgcc ggcagtgaaa ggtgccgtgg atgcgtttgt ccagaatgcc | 600 |
| cattttatg acaacggcga cgctcatggc aaggtgctga cgaggtgat catcacgatg | 660 |
| gacagtgctg gctacagca tgcctatctc gatgtagtga cgcagtggct gacccgttgg | 720 |
| aatgcgcaat atgccgagca ttggtatatg cgaaacgcag tcaatggtgt ctttactctt | 780 |
| ttgtttggcg gcagtggaa caatcagtac accagcctga ttggcgaaca gactgcgttg | 840 |
| gtgacggcct acaggcatt tgcgctgac cgtacgaaag tgaactcgcc aacggagttt | 900 |
| atggcggcca tgcggccag agaactgggg cggttagctc gctacacgga cgcgaccatt | 960 |
| gcgcctaaag tcacggaagg attaaccgcg atcttcggcc agtatccgtc ctatggcgat | 1020 |
| ggagatgcta tctggctggg ggcggcggat acggcctctt attatgctga ttgcagccag | 1080 |
| ttcaacatct gtggctttga agacgcgctg cgtgatgcgg cgctgaacca gacttttatc | 1140 |
| tgtagtgata cgattaaaat tcgctcacag gatatgtcgc aggcacagca tctcgcggct | 1200 |
| tgcgacaaaa tggcttatga agagtcattt ttccacacca cgcttgaaac cggtaatcag | 1260 |
| ccggtggctg atgatcataa tacgcagctg caggtgaata tttttaattc cgataccgat | 1320 |
| tacggtaaat atgccggtcc gatatttggg attgatacca caacggcgg tatgtacctc | 1380 |
| gagggaatc cggccaatgt gggcaatatt cccaatttca tcgcgtatga agccagctat | 1440 |
| gccaacccgg accattttgt ctggaatctt gagcacgagt acgtccacta tttggatggg | 1500 |
| cggttcaata tgtatggcga ttttggtacg cctaccgagc ttgtggtctg gtggagcgaa | 1560 |
| ggggtggccg agtatgtgtc gcgggtaaat gataatcctc aggcgattgc caccatccag | 1620 |

```
gatggtagca cgtacactct ggcgcaggtg tttgacacga cgtatgacgg ttttgatgtg    1680
gatcgcatct accgatgggg atatctggcg gtgcgattca tgtttgaacg tcatcctgat    1740
gaagttcaac gtatgctgag tgccacccga cagggacgct gggcagaata caaggcgatc    1800
attagcggtt gggcaaatca gtatcagtca gaatttgccc aatggaccga ggcgctggcg    1860
aagggcgaca gtggcgctgg gaacggtgag gggacaggct ccggtaatga agggggcggt    1920
gaatctggtg gtaataccgg cttgccggaa aactgcgcag tactgccaaa aatcagtgat    1980
gggcgtttag cactggatga agcggcctgt ctggccgaca cggcttcagc gtctgacgta    2040
ttgtggttca gtattccggc tgtcagtgaa tatcagacca ttgccattac ggcgggcaac    2100
gggactggcg acctgacgct ggaatacagt aacctgaatt ggccagatgg taccaatgtg    2160
caggcatcat cggcaaatat gggtaacagt gaatgcatta ttctggaaca tcaggcgaat    2220
tattggggat atctgaaagt ctcgggttcc tttgaaaatg cagcgttact ggtggaggct    2280
ggcagtaacc agtgtcgtca gtaa                                          2304
```

<210> SEQ ID NO 3
<211> LENGTH: 537
<212> TYPE: PRT
<213> ORGANISM: Grimontia hollisae

<400> SEQUENCE: 3

```
Ala Val Glu Gln Cys Asp Leu Ser Gln Phe Gln Thr Thr Ser Ser Asn
1               5                   10                  15

Gln Leu Met Ala Ala Ile Arg Gln Gln Gly Ala Ser Cys Val Asn Ala
            20                  25                  30

Leu Phe Ser Ala Asp Thr Gly Val Gln Glu Ala Ala Phe Ser Ser Asn
        35                  40                  45

His Met Tyr Asn Val Ala Gln Tyr Thr Arg Thr Leu Ala Gln Gln Tyr
    50                  55                  60

Ala Gly Gly Gly Ser Asp Glu Leu Glu Ala Leu Tyr Leu Tyr Leu Arg
65                  70                  75                  80

Ala Gly Tyr Tyr Ala Glu Phe Tyr Asn Ser Asn Ile Thr Phe Leu Ser
                85                  90                  95

Trp Val Thr Pro Ala Val Lys Gly Ala Val Asp Ala Phe Val Gln Asn
            100                 105                 110

Ala His Phe Tyr Asp Asn Gly Asp Ala His Gly Lys Val Leu Asn Glu
        115                 120                 125

Val Ile Ile Thr Met Asp Ser Ala Gly Leu Gln His Ala Tyr Leu Asp
    130                 135                 140

Val Val Thr Gln Trp Leu Thr Arg Trp Asn Ala Gln Tyr Ala Glu His
145                 150                 155                 160

Trp Tyr Met Arg Asn Ala Val Asn Gly Val Phe Thr Leu Leu Phe Gly
                165                 170                 175

Gly Gln Trp Asn Asn Gln Tyr Thr Ser Leu Ile Gly Glu Gln Thr Ala
            180                 185                 190

Leu Val Thr Ala Leu Gln Ala Phe Ala Leu Asp Arg Thr Lys Val Asn
        195                 200                 205

Ser Pro Thr Glu Phe Met Ala Ala Asn Ala Ala Arg Glu Leu Gly Arg
    210                 215                 220

Leu Ala Arg Tyr Thr Asp Ala Thr Ile Ala Pro Lys Val Thr Glu Gly
225                 230                 235                 240

Leu Thr Ala Ile Phe Gly Gln Tyr Pro Ser Tyr Gly Asp Gly Asp Ala
                245                 250                 255
```

Ile Trp Leu Gly Ala Ala Asp Thr Ala Ser Tyr Tyr Ala Asp Cys Ser
            260                 265                 270

Gln Phe Asn Ile Cys Gly Phe Glu Asp Ala Leu Arg Asp Ala Ala Leu
            275                 280                 285

Asn Gln Thr Phe Ile Cys Ser Asp Thr Ile Lys Ile Arg Ser Gln Asp
290                 295                 300

Met Ser Gln Ala Gln His Leu Ala Ala Cys Asp Lys Met Ala Tyr Glu
305                 310                 315                 320

Glu Ser Phe Phe His Thr Thr Leu Glu Thr Gly Asn Gln Pro Val Ala
                325                 330                 335

Asp Asp His Asn Thr Gln Leu Gln Val Asn Ile Phe Asn Ser Asp Thr
            340                 345                 350

Asp Tyr Gly Lys Tyr Ala Gly Pro Ile Phe Gly Ile Asp Thr Asn Asn
            355                 360                 365

Gly Gly Met Tyr Leu Glu Gly Asn Pro Ala Asn Val Gly Asn Ile Pro
370                 375                 380

Asn Phe Ile Ala Tyr Glu Ala Ser Tyr Ala Asn Pro Asp His Phe Val
385                 390                 395                 400

Trp Asn Leu Glu His Glu Tyr Val His Tyr Leu Asp Gly Arg Phe Asn
                405                 410                 415

Met Tyr Gly Asp Phe Gly Thr Pro Thr Glu Leu Val Val Trp Trp Ser
            420                 425                 430

Glu Gly Val Ala Glu Tyr Val Ser Arg Val Asn Asp Asn Pro Gln Ala
            435                 440                 445

Ile Ala Thr Ile Gln Asp Gly Ser Thr Tyr Thr Leu Ala Gln Val Phe
450                 455                 460

Asp Thr Thr Tyr Asp Gly Phe Asp Val Asp Arg Ile Tyr Arg Trp Gly
465                 470                 475                 480

Tyr Leu Ala Val Arg Phe Met Phe Glu Arg His Pro Asp Glu Val Gln
                485                 490                 495

Arg Met Leu Ser Ala Thr Arg Gln Gly Arg Trp Ala Glu Tyr Lys Ala
            500                 505                 510

Ile Ile Ser Gly Trp Ala Asn Gln Tyr Gln Ser Glu Phe Ala Gln Trp
            515                 520                 525

Thr Glu Ala Leu Ala Lys Gly Asp Ser
530                 535

<210> SEQ ID NO 4
<211> LENGTH: 559
<212> TYPE: PRT
<213> ORGANISM: Grimontia hollisae

<400> SEQUENCE: 4

Ala Val Glu Gln Cys Asp Leu Ser Gln Phe Gln Thr Thr Ser Ser Asn
1               5                   10                  15

Gln Leu Met Ala Ala Ile Arg Gln Gly Ala Ser Cys Val Asn Ala
            20                  25                  30

Leu Phe Ser Ala Asp Thr Gly Val Gln Glu Ala Phe Ser Ser Asn
                35                  40                  45

His Met Tyr Asn Val Ala Gln Tyr Thr Arg Thr Leu Ala Gln Gln Tyr
            50                  55                  60

Ala Gly Gly Gly Ser Asp Glu Leu Glu Ala Leu Tyr Leu Tyr Leu Arg
65                  70                  75                  80

Ala Gly Tyr Tyr Ala Glu Phe Tyr Asn Ser Asn Ile Thr Phe Leu Ser

```
                         85                  90                  95
Trp Val Thr Pro Ala Val Lys Gly Ala Val Asp Ala Phe Val Gln Asn
                100                 105                 110

Ala His Phe Tyr Asp Asn Gly Asp Ala His Gly Lys Val Leu Asn Glu
            115                 120                 125

Val Ile Ile Thr Met Asp Ser Ala Gly Leu Gln His Ala Tyr Leu Asp
        130                 135                 140

Val Val Thr Gln Trp Leu Thr Arg Trp Asn Ala Gln Tyr Ala Glu His
145                 150                 155                 160

Trp Tyr Met Arg Asn Ala Val Asn Gly Val Phe Thr Leu Leu Phe Gly
                165                 170                 175

Gly Gln Trp Asn Asn Gln Tyr Thr Ser Leu Ile Gly Glu Gln Thr Ala
            180                 185                 190

Leu Val Thr Ala Leu Gln Ala Phe Ala Leu Asp Arg Thr Lys Val Asn
        195                 200                 205

Ser Pro Thr Glu Phe Met Ala Ala Asn Ala Ala Arg Glu Leu Gly Arg
210                 215                 220

Leu Ala Arg Tyr Thr Asp Ala Thr Ile Ala Pro Lys Val Thr Glu Gly
225                 230                 235                 240

Leu Thr Ala Ile Phe Gly Gln Tyr Pro Ser Tyr Gly Asp Gly Asp Ala
                245                 250                 255

Ile Trp Leu Gly Ala Ala Asp Thr Ala Ser Tyr Tyr Ala Asp Cys Ser
            260                 265                 270

Gln Phe Asn Ile Cys Gly Phe Glu Asp Ala Leu Arg Asp Ala Ala Leu
        275                 280                 285

Asn Gln Thr Phe Ile Cys Ser Asp Thr Ile Lys Ile Arg Ser Gln Asp
        290                 295                 300

Met Ser Gln Ala Gln His Leu Ala Ala Cys Asp Lys Met Ala Tyr Glu
305                 310                 315                 320

Glu Ser Phe Phe His Thr Thr Leu Glu Thr Gly Asn Gln Pro Val Ala
                325                 330                 335

Asp Asp His Asn Thr Gln Leu Gln Val Asn Ile Phe Asn Ser Asp Thr
            340                 345                 350

Asp Tyr Gly Lys Tyr Ala Gly Pro Ile Phe Gly Ile Asp Thr Asn Asn
        355                 360                 365

Gly Gly Met Tyr Leu Glu Gly Asn Pro Ala Asn Val Gly Asn Ile Pro
370                 375                 380

Asn Phe Ile Ala Tyr Glu Ala Ser Tyr Ala Asn Pro Asp His Phe Val
385                 390                 395                 400

Trp Asn Leu Glu His Glu Tyr Val His Tyr Leu Asp Gly Arg Phe Asn
                405                 410                 415

Met Tyr Gly Asp Phe Gly Thr Pro Thr Glu Leu Val Val Trp Trp Ser
            420                 425                 430

Glu Gly Val Ala Glu Tyr Val Ser Arg Val Asn Asp Asn Pro Gln Ala
        435                 440                 445

Ile Ala Thr Ile Gln Asp Gly Ser Thr Tyr Thr Leu Ala Gln Val Phe
    450                 455                 460

Asp Thr Thr Tyr Asp Gly Phe Asp Val Asp Arg Ile Tyr Arg Trp Gly
465                 470                 475                 480

Tyr Leu Ala Val Arg Phe Met Phe Glu Arg His Pro Asp Glu Val Gln
                485                 490                 495

Arg Met Leu Ser Ala Thr Arg Gln Gly Arg Trp Ala Glu Tyr Lys Ala
            500                 505                 510
```

```
Ile Ile Ser Gly Trp Ala Asn Gln Tyr Gln Ser Glu Phe Ala Gln Trp
        515                 520                 525

Thr Glu Ala Leu Ala Lys Gly Asp Ser Gly Ala Gly Asn Gly Glu Gly
        530                 535                 540

Thr Gly Ser Gly Asn Glu Gly Gly Glu Ser Gly Gly Asn Thr
545                 550                 555

<210> SEQ ID NO 5
<211> LENGTH: 680
<212> TYPE: PRT
<213> ORGANISM: Grimontia hollisae

<400> SEQUENCE: 5

Ala Val Glu Gln Cys Asp Leu Ser Gln Phe Gln Thr Thr Ser Ser Asn
1               5                   10                  15

Gln Leu Met Ala Ala Ile Arg Gln Gln Gly Ala Ser Cys Val Asn Ala
            20                  25                  30

Leu Phe Ser Ala Asp Thr Gly Val Gln Glu Ala Ala Phe Ser Ser Asn
        35                  40                  45

His Met Tyr Asn Val Ala Gln Tyr Thr Arg Thr Leu Ala Gln Gln Tyr
    50                  55                  60

Ala Gly Gly Gly Ser Asp Glu Leu Glu Ala Leu Tyr Leu Tyr Leu Arg
65                  70                  75                  80

Ala Gly Tyr Tyr Ala Glu Phe Tyr Asn Ser Asn Ile Thr Phe Leu Ser
                85                  90                  95

Trp Val Thr Pro Ala Val Lys Gly Ala Val Asp Ala Phe Val Gln Asn
            100                 105                 110

Ala His Phe Tyr Asp Asn Gly Asp Ala His Gly Lys Val Leu Asn Glu
        115                 120                 125

Val Ile Ile Thr Met Asp Ser Ala Gly Leu Gln His Ala Tyr Leu Asp
    130                 135                 140

Val Val Thr Gln Trp Leu Thr Arg Trp Asn Ala Gln Tyr Ala Glu His
145                 150                 155                 160

Trp Tyr Met Arg Asn Ala Val Asn Gly Val Phe Thr Leu Leu Phe Gly
                165                 170                 175

Gly Gln Trp Asn Asn Gln Tyr Thr Ser Leu Ile Gly Glu Gln Thr Ala
            180                 185                 190

Leu Val Thr Ala Leu Gln Ala Phe Ala Leu Asp Arg Thr Lys Val Asn
        195                 200                 205

Ser Pro Thr Glu Phe Met Ala Ala Asn Ala Ala Arg Glu Leu Gly Arg
    210                 215                 220

Leu Ala Arg Tyr Thr Asp Ala Thr Ile Ala Pro Lys Val Thr Glu Gly
225                 230                 235                 240

Leu Thr Ala Ile Phe Gly Gln Tyr Pro Ser Tyr Gly Asp Gly Asp Ala
                245                 250                 255

Ile Trp Leu Gly Ala Ala Asp Thr Ala Ser Tyr Ala Asp Cys Ser
            260                 265                 270

Gln Phe Asn Ile Cys Gly Phe Glu Asp Ala Leu Arg Asp Ala Ala Leu
        275                 280                 285

Asn Gln Thr Phe Ile Cys Ser Asp Thr Ile Lys Ile Arg Ser Gln Asp
    290                 295                 300

Met Ser Gln Ala Gln His Leu Ala Ala Cys Asp Lys Met Ala Tyr Glu
305                 310                 315                 320

Glu Ser Phe Phe His Thr Thr Leu Glu Thr Gly Asn Gln Pro Val Ala
```

```
                         325                 330                 335
Asp Asp His Asn Thr Gln Leu Gln Val Asn Ile Phe Asn Ser Asp Thr
            340                 345                 350

Asp Tyr Gly Lys Tyr Ala Gly Pro Ile Phe Gly Ile Asp Thr Asn Asn
355                 360                 365

Gly Gly Met Tyr Leu Glu Gly Asn Pro Ala Asn Val Gly Asn Ile Pro
        370                 375                 380

Asn Phe Ile Ala Tyr Glu Ala Ser Tyr Ala Asn Pro Asp His Phe Val
385                 390                 395                 400

Trp Asn Leu Glu His Glu Tyr Val His Tyr Leu Asp Gly Arg Phe Asn
                405                 410                 415

Met Tyr Gly Asp Phe Gly Thr Pro Thr Glu Leu Val Val Trp Trp Ser
            420                 425                 430

Glu Gly Val Ala Glu Tyr Val Ser Arg Val Asn Asp Asn Pro Gln Ala
                435                 440                 445

Ile Ala Thr Ile Gln Asp Gly Ser Thr Tyr Thr Leu Ala Gln Val Phe
            450                 455                 460

Asp Thr Thr Tyr Asp Gly Phe Asp Val Asp Arg Ile Tyr Arg Trp Gly
465                 470                 475                 480

Tyr Leu Ala Val Arg Phe Met Phe Glu Arg His Pro Asp Glu Val Gln
                485                 490                 495

Arg Met Leu Ser Ala Thr Arg Gln Gly Arg Trp Ala Glu Tyr Lys Ala
            500                 505                 510

Ile Ile Ser Gly Trp Ala Asn Gln Tyr Gln Ser Glu Phe Ala Gln Trp
        515                 520                 525

Thr Glu Ala Leu Ala Lys Gly Asp Ser Gly Ala Gly Asn Gly Glu Gly
        530                 535                 540

Thr Gly Ser Gly Asn Glu Gly Gly Glu Ser Gly Gly Asn Thr Gly
545                 550                 555                 560

Leu Pro Glu Asn Cys Ala Val Leu Pro Lys Ile Ser Asp Gly Arg Leu
                565                 570                 575

Ala Leu Asp Glu Ala Ala Cys Leu Ala Asp Thr Ala Ser Ala Ser Asp
            580                 585                 590

Val Leu Trp Phe Ser Ile Pro Ala Val Ser Glu Tyr Gln Thr Ile Ala
        595                 600                 605

Ile Thr Ala Gly Asn Gly Thr Gly Asp Leu Thr Leu Gly Tyr Ser Asn
        610                 615                 620

Leu Asn Trp Pro Asp Gly Thr Asn Val Gln Ala Ser Ser Ala Asn Met
625                 630                 635                 640

Gly Asn Ser Glu Cys Ile Ile Leu Glu His Gln Ala Asn Tyr Trp Gly
                645                 650                 655

Tyr Leu Lys Val Ser Gly Ser Phe Glu Asn Ala Ala Leu Leu Val Glu
                660                 665                 670

Ala Gly Ser Asn Gln Cys Arg Gln
            675                 680

<210> SEQ ID NO 6
<211> LENGTH: 37
<212> TYPE: DNA
<213> ORGANISM: Artificial Sequence
<220> FEATURE:
<223> OTHER INFORMATION: primer

<400> SEQUENCE: 6
aaaccatggc tttcgctgcg gttgaacagt gtgatct                               37
```

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
aaaaagcttt tactgacgac actggttac                                   29

<210> SEQ ID NO 8
<211> LENGTH: 35
<212> TYPE: DNA
<213> ORGANISM: Artificial Sequence
<220> FEATURE:
<223> OTHER INFORMATION: primer

<400> SEQUENCE: 8
cccatggctt tcgctgcggt tgaacagtgt gatct                             35

<210> SEQ ID NO 9
<211> LENGTH: 34
<212> TYPE: DNA
<213> ORGANISM: Artificial Sequence
<220> FEATURE:
<223> OTHER INFORMATION: primer

<400> SEQUENCE: 9
catcctgtta agcttactgt cgcccttcgc cagc                              34

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
aagcttaaca ggatgcgggg                                              20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
agcgaaagcc atgggagcaa                                              20

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
cccatggctt tcgctgcggt tgaacagtgt gatct                             35

<210> SEQ ID NO 13
<211> LENGTH: 35
<212> TYPE: DNA
<213> ORGANISM: Artificial Sequence
<220> FEATURE:

<223> OTHER INFORMATION: primer

<400> SEQUENCE: 13
catcctgtta agcttaggta ttaccaccag attca                35

<210> SEQ ID NO 14
<211> LENGTH: 550
<212> TYPE: PRT
<213> ORGANISM: Grimontia hollisae

<400> SEQUENCE: 14

```
Ala Val Glu Gln Cys Asp Leu Ser Gln Phe Gln Thr Thr Ser Ser Asn
1               5                   10                  15

Gln Leu Met Ala Ala Ile Arg Gln Gln Gly Ala Ser Cys Val Asn Ala
            20                  25                  30

Leu Phe Ser Ala Asp Thr Gly Val Gln Glu Ala Ala Phe Ser Ser Asn
        35                  40                  45

His Met Tyr Asn Val Ala Gln Tyr Thr Arg Thr Leu Ala Gln Gln Tyr
    50                  55                  60

Ala Gly Gly Gly Ser Asp Glu Leu Glu Ala Leu Tyr Leu Tyr Leu Arg
65                  70                  75                  80

Ala Gly Tyr Tyr Ala Glu Phe Tyr Asn Ser Asn Ile Thr Phe Leu Ser
                85                  90                  95

Trp Val Thr Pro Ala Val Lys Gly Ala Val Asp Ala Phe Val Gln Asn
            100                 105                 110

Ala His Phe Tyr Asp Asn Gly Asp Ala His Gly Lys Val Leu Asn Glu
        115                 120                 125

Val Ile Ile Thr Met Asp Ser Ala Gly Leu Gln His Ala Tyr Leu Asp
    130                 135                 140

Val Val Thr Gln Trp Leu Thr Arg Trp Asn Ala Gln Tyr Ala Glu His
145                 150                 155                 160

Trp Tyr Met Arg Asn Ala Val Asn Gly Val Phe Thr Leu Leu Phe Gly
                165                 170                 175

Gly Gln Trp Asn Asn Gln Tyr Thr Ser Leu Ile Gly Glu Gln Thr Ala
            180                 185                 190

Leu Val Thr Ala Leu Gln Ala Phe Ala Leu Asp Arg Thr Lys Val Asn
        195                 200                 205

Ser Pro Thr Glu Phe Met Ala Ala Asn Ala Ala Arg Glu Leu Gly Arg
    210                 215                 220

Leu Ala Arg Tyr Thr Asp Ala Thr Ile Ala Pro Lys Val Thr Glu Gly
225                 230                 235                 240

Leu Thr Ala Ile Phe Gly Gln Tyr Pro Ser Tyr Gly Asp Gly Asp Ala
                245                 250                 255

Ile Trp Leu Gly Ala Ala Asp Thr Ala Ser Tyr Tyr Ala Asp Cys Ser
            260                 265                 270

Gln Phe Asn Ile Cys Gly Phe Glu Asp Ala Leu Arg Asp Ala Ala Leu
        275                 280                 285

Asn Gln Thr Phe Ile Cys Ser Asp Thr Ile Lys Ile Arg Ser Gln Asp
    290                 295                 300

Met Ser Gln Ala Gln His Leu Ala Ala Cys Asp Lys Met Ala Tyr Glu
305                 310                 315                 320

Glu Ser Phe Phe His Thr Thr Leu Glu Thr Gly Asn Gln Pro Val Ala
                325                 330                 335

Asp Asp His Asn Thr Gln Leu Gln Val Asn Ile Phe Asn Ser Asp Thr
            340                 345                 350
```

```
Asp Tyr Gly Lys Tyr Ala Gly Pro Ile Phe Gly Ile Asp Thr Asn Asn
            355                 360                 365

Gly Gly Met Tyr Leu Glu Gly Asn Pro Ala Asn Val Gly Asn Ile Pro
    370                 375                 380

Asn Phe Ile Ala Tyr Glu Ala Ser Tyr Ala Asn Pro Asp His Phe Val
385                 390                 395                 400

Trp Asn Leu Glu His Glu Tyr Val His Tyr Leu Asp Gly Arg Phe Asn
                405                 410                 415

Met Tyr Gly Asp Phe Gly Thr Pro Thr Glu Leu Val Val Trp Trp Ser
            420                 425                 430

Glu Gly Val Ala Glu Tyr Val Ser Arg Val Asn Asp Asn Pro Gln Ala
                435                 440                 445

Ile Ala Thr Ile Gln Asp Gly Ser Thr Tyr Thr Leu Ala Gln Val Phe
            450                 455                 460

Asp Thr Thr Tyr Asp Gly Phe Asp Val Asp Arg Ile Tyr Arg Trp Gly
465                 470                 475                 480

Tyr Leu Ala Val Arg Phe Met Phe Glu Arg His Pro Asp Glu Val Gln
                485                 490                 495

Arg Met Leu Ser Ala Thr Arg Gln Gly Arg Trp Ala Glu Tyr Lys Ala
            500                 505                 510

Ile Ile Ser Gly Trp Ala Asn Gln Tyr Gln Ser Glu Phe Ala Gln Trp
            515                 520                 525

Thr Glu Ala Leu Ala Lys Gly Asp Ser Gly Ala Gly Asn Gly Glu Gly
            530                 535                 540

Thr Gly Ser Gly Asn Glu
545                 550

<210> SEQ ID NO 15
<211> LENGTH: 555
<212> TYPE: PRT
<213> ORGANISM: Grimontia hollisae

<400> SEQUENCE: 15

Ala Val Glu Gln Cys Asp Leu Ser Gln Phe Gln Thr Thr Ser Ser Asn
1               5                   10                  15

Gln Leu Met Ala Ala Ile Arg Gln Gln Gly Ala Ser Cys Val Asn Ala
            20                  25                  30

Leu Phe Ser Ala Asp Thr Gly Val Gln Glu Ala Ala Phe Ser Ser Asn
        35                  40                  45

His Met Tyr Asn Val Ala Gln Tyr Thr Arg Thr Leu Ala Gln Gln Tyr
    50                  55                  60

Ala Gly Gly Gly Ser Asp Glu Leu Glu Ala Leu Tyr Leu Tyr Leu Arg
65                  70                  75                  80

Ala Gly Tyr Tyr Ala Glu Phe Tyr Asn Ser Asn Ile Thr Phe Leu Ser
                85                  90                  95

Trp Val Thr Pro Ala Val Lys Gly Ala Val Asp Ala Phe Val Gln Asn
            100                 105                 110

Ala His Phe Tyr Asp Asn Gly Asp Ala His Gly Lys Val Leu Asn Glu
        115                 120                 125

Val Ile Ile Thr Met Asp Ser Ala Gly Leu Gln His Ala Tyr Leu Asp
    130                 135                 140

Val Val Thr Gln Trp Leu Thr Arg Trp Asn Ala Gln Tyr Ala Glu His
145                 150                 155                 160

Trp Tyr Met Arg Asn Ala Val Asn Gly Val Phe Thr Leu Leu Phe Gly
```

```
                165                 170                 175
Gly Gln Trp Asn Asn Gln Tyr Thr Ser Leu Ile Gly Glu Gln Thr Ala
            180                 185                 190
Leu Val Thr Ala Leu Gln Ala Phe Ala Leu Asp Arg Thr Lys Val Asn
        195                 200                 205
Ser Pro Thr Glu Phe Met Ala Ala Asn Ala Ala Arg Glu Leu Gly Arg
    210                 215                 220
Leu Ala Arg Tyr Thr Asp Ala Thr Ile Ala Pro Lys Val Thr Glu Gly
225                 230                 235                 240
Leu Thr Ala Ile Phe Gly Gln Tyr Pro Ser Tyr Gly Asp Gly Asp Ala
                245                 250                 255
Ile Trp Leu Gly Ala Ala Asp Thr Ala Ser Tyr Tyr Ala Asp Cys Ser
            260                 265                 270
Gln Phe Asn Ile Cys Gly Phe Glu Asp Ala Leu Arg Asp Ala Ala Leu
        275                 280                 285
Asn Gln Thr Phe Ile Cys Ser Asp Thr Ile Lys Ile Arg Ser Gln Asp
    290                 295                 300
Met Ser Gln Ala Gln His Leu Ala Ala Cys Asp Lys Met Ala Tyr Glu
305                 310                 315                 320
Glu Ser Phe Phe His Thr Thr Leu Glu Thr Gly Asn Gln Pro Val Ala
                325                 330                 335
Asp Asp His Asn Thr Gln Leu Gln Val Asn Ile Phe Asn Ser Asp Thr
            340                 345                 350
Asp Tyr Gly Lys Tyr Ala Gly Pro Ile Phe Gly Ile Asp Thr Asn Asn
        355                 360                 365
Gly Gly Met Tyr Leu Glu Gly Asn Pro Ala Asn Val Gly Asn Ile Pro
    370                 375                 380
Asn Phe Ile Ala Tyr Glu Ala Ser Tyr Ala Asn Pro Asp His Phe Val
385                 390                 395                 400
Trp Asn Leu Glu His Glu Tyr Val His Tyr Leu Asp Gly Arg Phe Asn
                405                 410                 415
Met Tyr Gly Asp Phe Gly Thr Pro Thr Glu Leu Val Val Trp Trp Ser
            420                 425                 430
Glu Gly Val Ala Glu Tyr Val Ser Arg Val Asn Asp Asn Pro Gln Ala
        435                 440                 445
Ile Ala Thr Ile Gln Asp Gly Ser Thr Tyr Thr Leu Ala Gln Val Phe
    450                 455                 460
Asp Thr Thr Tyr Asp Gly Phe Asp Val Asp Arg Ile Tyr Arg Trp Gly
465                 470                 475                 480
Tyr Leu Ala Val Arg Phe Met Phe Glu Arg His Pro Asp Glu Val Gln
                485                 490                 495
Arg Met Leu Ser Ala Thr Arg Gln Gly Arg Trp Ala Glu Tyr Lys Ala
            500                 505                 510
Ile Ile Ser Gly Trp Ala Asn Gln Tyr Gln Ser Glu Phe Ala Gln Trp
        515                 520                 525
Thr Glu Ala Leu Ala Lys Gly Asp Ser Gly Ala Gly Asn Gly Glu Gly
    530                 535                 540
Thr Gly Ser Gly Asn Glu Gly Gly Glu Ser
545                 550                 555
```

GRIMONITIA-HOLLISAE-DERIVED RECOMBINANT COLLAGENASE AND ENZYME AGENT FOR CELL AND TISSUE DISSOCIATION

TECHNICAL FIELD

The present disclosure relates to a *Grimontia-hollisae*-derived recombinant collagenase, and an enzyme agent for cell and tissue dissociation.

BACKGROUND ART

The pancreas contains exocrine glands that secret digestive enzymes into the duodenum and the pancreatic islets which are endocrine glands. A treatment whereby the pancreatic islets, which play an important role in regulation of blood glucose concentration, are separated from the pancreas, purified, and transplanted to patients with insulin-dependent type 1 diabetes mellitus and the like is referred to as pancreatic islet transplantation. Because the pancreatic islets can be infused into the body in a manner of drip infusion, the pancreatic islet transplantation is minimally invasive and physical burden on the patient is lower.

Meanwhile, the exocrine gland accounts for about 90% of the pancreas; and technique for separating the pancreatic islets are difficult ones and exhibit an extremely low success rate. Currently, as an enzyme agent for cell and tissue dissociation, a mixture of subtypes called collagenase H (ColH) and collagenase G (ColG), both of which are derived from *Clostridium histolyticum*, is used for separation of the pancreatic islets from the pancreas in a practical clinical setting. However, because the tissue composition of the pancreas varies in age and degree of ponderal index, the separation of the pancreatic islets succeeds only when an enzyme agent for the pancreatic islet separation is compatible with pancreatic tissues provided.

The above ColH and ColG are multidomain proteins having plural domain structures and the activity thereof is associated with a combination and relative arrangement of the domains (Non Patent Literature 1). According to Non Patent Literature 1, collagenases derived from the genus *Clostridium* contain, in common, three domains namely a catalytic domain (hereinafter, may also be referred to as CD), a polycystic kidney disease-like domain (hereinafter, may also be referred to as PKD), and a collagen-binding domain (hereinafter, may also be referred to as CBD). ColH has a domain structure that is composed of one CD, two PKDs, and one CBD and represented by CD-PKD-PKD-CBD; and ColG has a domain structure that is composed of one CD, one PKD, and two CBDs and represented by CD-PKD-CBD-CBD. Non Patent Literature 1 discloses that calcium binds to the N terminal side of CBD and the N terminal portion of the domain undergoes structural change when calcium comes off; that calcium is important for collagen binding; that calcium contributes to stabilization of ColH; and the like.

Meanwhile, as for a microorganism-derived collagenase with a high specific activity, a *Grimontia-hollisae*-derived collagenase is available (Non Patent Literature 2). It is a collagenase that contains a prepro region, a catalytic domain, a linker region, and a prepeptidase C terminal domain (hereinafter, also referred to as PPC) and has a molecular weight of 84 kDa; and the result of BLAST search has indicated that it exhibits a low homology with ColH and ColG. Further, it is difficult to inexpensively obtain the *Grimontia-hollisae*-derived collagenase; and in light of this problem, a method of developing technique for production of such a collagenase using a genetic engineering technique has also been suggested (Patent Literature 1). This Patent Literature 1 describes a method of preparing a bacmid pCC1BAC-2 that contains a gene for the entire coding region of *Grimontia-hollisae*-derived collagenase and a method of preparing a *Brevibacillus choshinensis* recombinant using the bacmid pCC1BAC-2 to thereby produce the *Grimontia-hollisae*-derived collagenase.

CITATION LIST

Patent Literature

Patent Literature 1: Unexamined Japanese Patent Application Kokai Publication No. 2010-263880

Non Patent Literature

Non Patent Literature 1: Naomi Ohbayashi and Kazutaka Murayama, "Analysis of intramolecular conformational changes of multidomain protein collagenases", Journal of Japanese Biochemical Society or SEIKAGAKU, Vol. 85, No. 8, pp. 692-699, 2013

Non Patent Literature 2: Teramura Naoko etc, Cloning of a Novel Collagenase Gene from the Gram-Negative Bacterium *Grimontia* (*Vibrio*) *hollisae* 1706B and Its Efficient Expression in *Brevibacillus choshinensis*, Journal of Bacteriology, June 2011 vol. 193 no. 12 p. 3049-3056.

SUMMARY OF INVENTION

Technical Problem

In a practical clinical setting including pancreatic islet transplantation, a mixture of ColH and ColG, both of which are easily available, is used. Yet, the domain structure differs between ColH and ColG; and the performance varies depending on a mix ratio of ColH with ColG, resulting in unstable activities. Meanwhile, it is not easy to adjust the mix ratio, which contributes to a lower success rate of the pancreatic islet separation. It has therefore been deeply desired that an enzyme agent for cell and tissue dissociation be developed, which enzyme agent is not required to be mixed and has a stable activity.

Meanwhile, the *Grimontia-hollisae*-derived collagenase disclosed in the above-Non Patent Literature 1 has a high specific activity; and Patent Literature 1 also discloses a method of producing a *Grimontia-hollisae*-derived collagenase employing genetic engineering. However, the *Grimontia-hollisae*-derived collagenase has had in some cases a varying specific activity. If the specific activity is different for each production lot, it ends up being difficult to use a different lot in the same protocol. In addition, if the activity decreases with time, an amount used varies and thus the yield of cells varies; or cells may become stressed when an excessive breakdown treatment is carried out. Meanwhile, details for the domain of *Grimontia-hollisae*-derived collagenase have not been elucidated; and the cause of reduction in the specific activity has not been unknown either. It has therefore been deeply desired that a recombinant collagenase be developed, which recombinant collagenase is derived from a *Grimontia-hollisae*-derived collagenase with a stable specific activity.

Further, the demand for cell separation is not limited to the pancreatic islets. In addition to the liver, the heart, the lung, the kidney, the spleen, the adrenal gland, and muscles;

glandular tissues such as the thyroid gland, the salivary gland, the parotid gland acinus, and mammary tissues; bone tissues such as bones and cartilages; and cells such as endothelial cells, epithelial cells, and adipose tissues may also be separated and thereafter used. In order to keep separated cells' engraftment capability and the like well, it is important that the cells are less damaged and have a high engraftment rate. It has therefore been desired that a cell and tissue dissociation agent be developed, which cell and tissue dissociation agent is very much capable of separating a variety of cells and exhibits an excellent engraftment rate.

The success rate of pancreatic islet transplantation depends also the amount of enzyme left in the separated pancreatic islets; and a more amount of the enzyme left leads to a lower transplantation rate. It is preferred that less enzymes be left after cell washing; and the same is applied for other organs and cells. Accordingly, there is a need for a novel collagenase capable of rapidly dissociating from tissues after washing the tissue or of decreasing the collagenase activity when the collagenase is left in the washed tissue to avoid or reduce cell damage.

Under these circumstances, an object of the present disclosure is to provide a novel *Grimontia-hollisae*-derived recombinant collagenase with an excellent collagenase activity and a stable specific activity.

Further, an object of the present disclosure is to provide an enzyme agent for cell and tissue dissociation that utilizes the thus obtained novel *Grimontia-hollisae*-derived recombinant collagenase.

Solution to Problem

The present inventors investigated the gene of a *Grimontia-hollisae*-derived collagenase in detail and found out that its prepro region is a secretion signal sequence, that a high collagenase activity is retained even when PPC is removed, that a stable collagenase activity can be maintained when the third amino acid residue from the C terminal of its linker region sequence is a glycine, which linker region sequence connects CD with PPC, thereby completing the present disclosure.

That is, the present disclosure provides a recombinant collagenase that is derived from *Grimontia hollisae*-derived collagenase comprising, from N terminal to C terminal, a collagenase catalytic domain, a linker region sequence, and a prepeptidase C terminal domain, which *Grimontia hollisae*-derived recombinant collagenase does not comprise at least the prepeptidase C terminal domain.

Further, the present disclosure provides the above *Grimontia-hollisae*-derived recombinant collagenase characterized in that the linker region of the recombinant collagenase is a linker fragment cleaved at any amide bonds in the linker region of the *Grimontia-hollisae*-derived collagenase.

Further, the present disclosure provides the above *Grimontia-hollisae*-derived recombinant collagenase characterized in that the linker fragment has a glycine as the third amino acid residue from the C terminal.

Further, the present disclosure provides the above *Grimontia-hollisae*-derived recombinant collagenase characterized in that the linker fragment is obtained by cleavage between $Y_1$ and $G_2$ in an amino acid sequence represented by -$G_1$-$X_1$-$Y_1$-$G_2$-$X_2$-$Y_2$- (wherein $G_1$ and $G_2$ represent glycine; and $X_1$, $Y_1$, $X_2$, and $Y_2$ may be same or different and represent an amino acid residue) in the linker region of the *Grimontia-hollisae*-derived collagenase.

Further, the present disclosure provides the above *Grimontia-hollisae*-derived recombinant collagenase characterized in that C terminal of the linker fragment is any of -Gly-Asp-Ser, -Gly-Asn-Glu, -Gly-Glu-Ser, or -Gly-Asn-Thr.

Further, the present disclosure provides an enzyme agent for cell and tissue dissociation that contains the above recombinant collagenase.

Further, the present disclosure provides the above enzyme agent for cell and tissue dissociation characterized by being used for separation of one or more cells selected from the group consisting of pancreatic islet, liver, heart, lung, kidney, spleen, adrenal gland, muscle, thyroid gland, salivary gland, parotid gland acini, mammary tissue, bone, cartilage, endothelial cell, epithelial cell, adipose tissue and fibroblast.

Advantageous Effects of Invention

According to the present disclosure, a *Grimontia-hollisae*-derived recombinant collagenase with a stable specific activity is provided. Culturing an isolated organ with an enzyme agent for cell and tissue dissociation that contains this recombinant collagenase enables cells to be efficiently separated.

BRIEF DESCRIPTION OF DRAWINGS

FIG. 6A shows the result for the number of the pancreatic islets and FIG. 6B shows the result for IEQ;

FIG. 8 is a figure showing the results of Example 6 and a figure showing temporal variation in the blood glucose level in the STZ-induced diabetic mice that were transplanted with the pancreatic islets and the mice that were not transplanted and the result of staining of the extracted kidney and tissues that underwent pancreatic islet transplantation; FIG. 8A shows the result of changes in the blood glucose level in the mice and FIG. 8B shows the result of staining of the extracted kidney and tissues that underwent pancreatic islet transplantation;

FIG. 10 is a figure showing the results of Example 8 and Comparative Example 2 and FIG. 10A represents the result showing the ability of the recombinant 62 kDa collagenase to bind to collagen fibers and FIG. 10B represents the result showing the ability of the collagenase derived from *Clostridium histolyticum* (liberase) to bind to collagen fibers;

DESCRIPTION OF EMBODIMENTS

A first of the present disclosure is a recombinant collagenase that is derived from a *Grimontia-hollisae*-derived collagenase comprising from N terminal to C terminal, a collagenase catalytic domain, a linker region sequence, and a prepeptidase C terminal domain, which recombinant collagenase is characterized by not containing at least the prepeptidase C terminal domain. The present disclosure will now be described in detail below.

(1) *Grimontia hollisae*

*Clostridium* (*Clostridium* sp.), *Vibrio* (*Vibrio* sp.), *Bacillus* (*Bacillus* sp.), *Streptomyces* (*Streptomyces* sp.), and the like are known as microorganisms that can produce a collagenase, and the collagenase used in the present disclosure is derived from *Grimontia* (*Grimontia* sp.). It is to be noted that *Grimontia hollisae* is available as, for example, ATCC No. 33564 and ATCC No. 33565.

(2) *Grimontia-Hollisae*-Derived Collagenase

Figure 1:
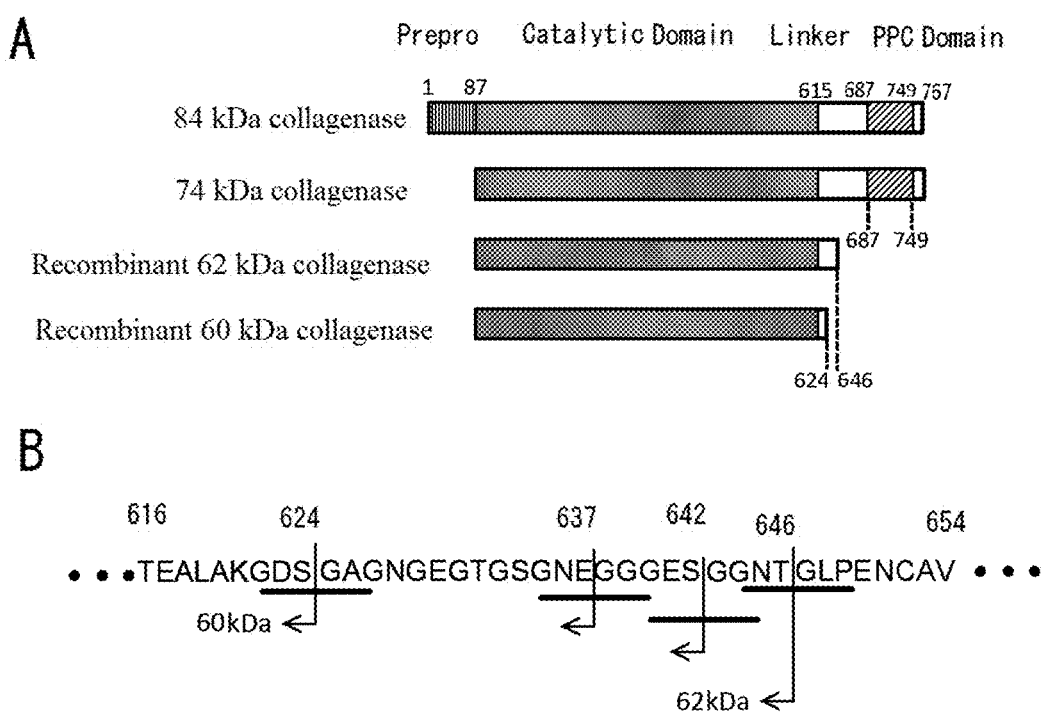
FIG. 1 is a figure illustrating the domain structure and the sequence of the linker region of the *Grimontia-hollisae*-derived collagenase and the amino acid sequence encoding the recombinant 60 kDa collagenase and the recombinant 62 kDa collagenase.

The domain structure of the amino acid sequence of *Grimontia-hollisae*-derived collagenase is shown in FIG. 1A. The domain structure represented by the "84 kDa collagenase" shows a domain structure of the entire coding sequence of the *Grimontia-hollisae*-derived collagenase. From the N terminal to the C terminal, amino acids numbered 1 to 87 is a prepro region; amino acids numbered 88 to 615 is a catalytic domain region (CD), amino acids numbered 616 to 687 is a linker region; and amino acids numbered 688 to 749 is a PPC domain region (PPC). This collagenase is composed of 767 amino acids and its molecular weight is 84 kDa. The amino acid sequence of a *Grimontia-hollisae*-derived collagenase 1706B strain is shown in SEQ ID NO: 1 and the DNA sequence of the entire coding region thereof is shown in SEQ ID NO: 2 as an example of the *Grimontia-hollisae*-derived collagenase. It is to be noted that the above prepro region has been found to be a secretion signal sequence. It is not, however, clear that at what stage in the translation the secretion signal sequence is released. In the present disclosure, both a collagenase having the prepro region and a collagenase that lacks the prepro region are regarded as the *Grimontia-hollisae*-derived collagenase. The molecular weight of the *Grimontia-hollisae*-derived collagenase that lacks the prepro region is 74 kDa. This domain structure is shown as the "74 kDa collagenase" in FIG. 1A.

(3) *Grimontia-Hollisae*-Derived Recombinant Collagenase

The *Grimontia-hollisae*-derived recombinant collagenase of the present disclosure is derived from *Grimontia hollisae*. It may have any domain structure as long as PPC is not contained at least. For example, a recombinant collagenase composed of a prepro region, CD, and a linker region from the N terminal to the C terminal, which is obtained by lacking an amino acid sequence at the 688th position and later from the domain structure shown in the above 84 kDa collagenase in FIG. 1A. In addition, a recombinant collagenase that lacks the prepro region and is composed of CD and the linker region may also be used. As shown in the example described later, it has been found that, even when PPC is deleted, a high collagenase activity is exerted and, at the same time, the collagenase activity is stable. Further, the *Grimontia-hollisae*-derived recombinant collagenase of the present disclosure, as shown in the example described later, the collagenase activity after washing decreases to reduce cell damage.

The linker region of the *Grimontia-hollisae*-derived recombinant collagenase of the present disclosure may also be a linker fragment in which a part of its amino acid sequence is deleted. The term "linker fragment" in the present disclosure refers to one obtained by cleaving at any of the amide bonds in the linker region. For example, in the domain structure shown in the 84 kDa collagenase in FIG. 1A, the linker fragment is one obtained by cleaving at any of the amide bonds in the linker region composed of the amino acids from the 616th to 687th positions. The "recombinant 62 kDa collagenase" in FIG. 1A is an example that has a linker fragment composed of 31 amino acids from the 616th to 646th positions; and the "recombinant 60 kDa collagenase" in FIG. 1A is an example that has a linker fragment composed of 9 amino acids from the 616th to 624th positions.

The above linker fragment preferably has a glycine as the third amino acid residue from the C terminal. As shown in the example described later, the recombinant collagenase with a glycine as the third amino acid residue from the C terminal exhibits a collagenase activity with excellent stability. The above linker region contains, as shown in SEQ ID NO: 1, the amino acid sequence represented by $-G_1-X_1-Y_1-G_2-X_2-Y_2-$ (wherein $G_1$ and $G_2$ represent glycine; and $X_1$, $Y_1$, $X_2$, and $Y_2$ may be same or different and represent an amino acid residue). The cleavage of the linker region between $Y_1$ and $G_2$ in the above amino acid sequence results in the third amino acid from the C terminal being glycine.

For the sake of convenience, FIG. 1B shows the amino acid sequence of a part of the linker region of the "84 kDa collagenase" shown in FIG. 1A.

"60 kDa" represents the C terminal of the recombinant 60 kDa collagenase" and "62 kDa" represents the C terminal of "recombinant 62 kDa collagenase. The C terminal of the recombinant 60 kDa collagenase is obtained by cleaving between S and G in the sequence represented by -GDSGAG- of the linker region; and the recombinant 62 kDa collagenase is obtained by cleaving between T and G in the sequence represented by -GNTGLP-. As a result, both come to have a glycine as the third amino acid residue from the C terminal. It is to be noted that the cleavage of the $-G_1X_1Y_1G_2X_2Y_2-$ in the linker region may, as shown in FIG. 1B, be the cleavage between the 637th position and the 638th position or between the 642nd position and the 643rd position.

The C terminal of the recombinant collagenase of the present disclosure is preferably a linker fragment obtained by cleaving between $Y_1$ and $G_2$ in the amino acid sequence represented by the -G$_1$-X$_1$-Y$_1$-G$_2$-X$_2$-Y$_2$- (wherein G$_1$ and G$_2$ represent glycine; and X$_1$, Y$_1$, X$_2$, and Y$_2$ may be same or different and represent an amino acid residue). Because the specific activity of the recombinant collagenase having a linker fragment obtained by the cleavage between Y$_1$ and G$_2$ is stable over a long period of time. Therefore, the C terminal is preferably any of, for example, -GDS, -GNE, -GES, and -GNT. In the sequence shown in FIG. 1B, the cleavage between Y$_1$ and G$_2$ in the amino acid sequence results in the C terminal being the above sequence.

SEQ ID NO: 3 represents the amino acid sequence of the recombinant 60 kDa collagenase composed of an amino acid sequence numbered 88 to 624, and SEQ ID NO: 4 represents the amino acid sequence of the recombinant 62 kDa collagenase composed of an amino acid sequence numbered 88 to 646, both of which lack prepro region and PPC and has the prescribed linker fragment. In addition, SEQ ID NO: 5 represents the amino acid sequence numbered 88 to 767 as 74 kDa collagenase, which is obtained by deleting the prepro region from the 84 kDa collagenase.

It has not completely understood why the recombinant collagenase of the present disclosure exhibits an excellent storage stability. There is possibility that PPC per se has a collagen binding ability and auxiliarily contributes to CD's collagenase activity, because when the specific activity and stability of the 74 kDa collagenase having PPC and the recombinant collagenase not having PPC are evaluated, the 74 kDa collagenase is found to have a higher specific activity. It is presumed that the recombinant collagenase of the present disclosure has a stable collagenase activity and increased property of separating from tissues at washing by lacking PPC, because the PPC auxiliarily contributes to the collagenase activity. Incidentally, the recombinant collagenase of the present disclosure may also lack the linker region as long as it lacks PPC.

(4) Method of Producing the Recombinant Collagenase.

A DNA for transformation used for preparation of the recombinant collagenase of the present disclosure is one encoding at least the amino acid sequence of CD, and more preferably one encoding the amino acid sequence of CD and a part of linker region. One further having the amino acid sequence of the prepro region at the N terminal side may also be used. As for the C terminal of the linker region, one obtained by cleaving between Y$_1$ and G$_2$ in the sequence represented by -G$_1$X$_1$Y$_1$G$_2$X$_2$Y$_2$- contained in the linker region sequence is suitably used. As a DNA for preparing a recombinant collagenase which does not contain PPC and has a glycine at the third position from the C terminal, one encoding the amino acid sequence represented by (I) shown below can be used.

```
Formula (I):
AVEQCDLSQFQTTSSNQLMAAIRQQGASCVNALFSADTGVQEAAFSSNHM

YNVAQYTRTLAQQYAGGGSDELEALYLYLRAGYYAEFYNSNITFLSWVTP

AVKGAVDAFVQNAHFYDNGDAHGKVLNEVIITMDSAGLQHAYLDVVTQWL

TRWNAQYAEHWYMRNAVNGVFTLLFGGQWNNQYTSLIGEQTALVTALQAF

ALDRTKVNSPTEFMAANAARELGRLARYTDATIAPKVTEGLTAIFGQYPS

YGDGDAIWLGAADTASYYADCSQFNICGFEDALRDAALNQTFICSDTIKI

RSQDMSQAQHLAACDKMAYEESFFHTTLETGNQPVADDHNTQLQVNIFNS

DTDYGKYAGPIFGIDTNNGGMYLEGNPANVGNIPNFIAYEASYANPDHFV
```

```
-continued
WNLEHEYVHYLDGRFNMYGDFGTPTELVVWWSEGVAEYVSRVNDNPQAIA

TIQDGSTYTLAQVFDTTYDGFDVDRIYRWGYLAVRFMFERHPDEVQRMLS

ATRQGRWAEYKAIISGWANQYQSEFAQW-X
``` wherein X is a polypeptide represented by TEALAK-GDSGAGNGEGTGSGNEGGG ESGGNT or TEALAK-GDS. SEQ ID NO: 3 is the amino acid sequence when X represents TEALAKGDS; and SEQ ID NO: 4 is the amino acid sequence when X represents TEALAKGD SGAGNGEGTGSGNEGGGESGGNT. It is to be noted that alphabetical symbols used in the formula denote the following amino acids. A: alanine, C: cysteine, D: aspartic acid, E: glutamic acid, F: phenyl alanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan, and Y: tyrosine.

To prepare the recombinant collagenase of the present disclosure, it is simply required a preparation of a recombinant vector containing a DNA encoding the above amino acid sequence, preparation of host cells with collagenase activity by transforming the host cells with the recombinant vector, and culture of the host cells to generate a gene product with the collagenase activity. Such a method of producing a recombinant protein can be carried out by employing techniques in genetic engineering. For example, a clone containing a *Grimontia hollisae*-derived collagenase gene is selected from a genome library of *Grimontia hollisae*; amplification is carried out using Expand High Fidelity PCR System (Roche) with the clone as a template to add an Nco I site on the 5' side and a Hind III site on the 3' side of a DNA fragment encoding the SEQ ID NO: 3 or SEQ ID NO: 4 respectively; the amplified fragment is treated with Nco I and Hind III to obtain the DNA fragment; the recovered DNA fragment is inserted into a plasmid vector to prepare a recombinant plasmid; the recombinant plasmid is used to transform, for example, a *Brevibacillus choshinensis* HPD31-SP3 strain or the like, thereby preparing a *Brevibacillus choshinensis* recombinant. Alternatively, a DNA fragment may be prepared and amplified as a clone containing the *Grimontia-hollisae*-derived collagenase gene as a template, which DNA fragment is a DNA fragment encoding the SEQ ID NO: 3 or SEQ ID NO: 4 with 15 bp-sequences homologous to both termini of linear expression vector to be inserted being added to both the termini: and this amplified DNA fragment and the linear expression vector may be mixed and introduced to a *Brevibacillus choshinensis* HPD31-SP3 strain or the like by New Tris-PEG method, thereby preparing a recombinant plasmid and a recombinant. Culturing the thus obtained *Brevibacillus choshinensis* recombinant enables a *Grimontia hollisae*-derived collagenase gene product to be generated in a culture supernatant.

A method of collecting and purifying a recombinant collagenase from the culture medium can be carried out in accordance with known means of collecting and purifying an enzyme. Examples thereof include a method comprising subjecting the culture to centrifugation, filtration, or the like to separate bacterial cells; and purifying the enzyme from the culture filtrate using a usual separation means such as, for example, organic solvent precipitation, salting out, concentration by ultrafiltration membrane via column chromatography or the like.

It is to be noted that, as for the *Grimontia-hollisae*-derived recombinant collagenase of the present disclosure, the recombinant collagenase may be produced from host cells transformed with DNA not originally containing the prepro region; or the recombinant collagenase may be produced from host cells transformed with DNA containing the prepro region, followed by release of the prepro region in the course of or after the translation.

(5) Enzyme Agent for Cell and Tissue Dissociation

The recombinant collagenase obtained by the production method of the present disclosure can be used in the same manner as conventional collagenases, and can, for example, be used as an enzyme agent for cell and tissue dissociation. Examples of isolated organs for separating cells include, pancreatic islet, liver, heart, lung, kidney, spleen, adrenal gland, muscles, as well as glandular tissues such as thyroid gland, salivary gland, parotid gland acinus, and mammary tissues; bone tissues such as bones and cartilages; endothelial cells; epithelial cells; adipose tissues and fibroblasts. The use of the enzyme agent is not limited to the isolated organ and is suitable for separation of cultured cells from a collagen gel. Because the recombinant collagenase obtained in the present disclosure, in particular, has a stable specific activity, it is suitably used as an enzyme agent for cell and tissue dissociation to separate pancreatic islets from an isolated pancreas. As shown in the example described later, it has a lower collagenase activity for washed tissues and causes less cell damage.

The enzyme agent for cell and tissue dissociation used in the present disclosure can further contain other components including metalloproteases, serine proteases, cysteine proteases and other components. Examples of metalloproteases include thermolysin, Dispase, and a neutral protease derived from *Clostridium histolyticum*. Examples of serine proteases include trypsin and elastase; and examples of cysteine proteases include chymopapain.

(6) Method of Separating Cells

The enzyme agent for cell and tissue dissociation of the present disclosure are added to isolated organs or animal tissues and incubated for a prescribed period. When an isolated organ is incubated in culture medium with the enzyme agent for cell and tissue dissociation or further added other components, it is possible to degrade extracellular matrices or cell junction in the isolated organ to dissociated cells from the organ. In cases where the cells dissociated from the tissue float in the culture medium, it is simply required to collect the separated cell from the culture medium via filtration or centrifugation.

In the present disclosure, the pancreatic islets can be separated when the pancreas is used as an isolated organ. The incubating isolated pancreas with the collagenase enables the pancreatic islets to be freed from the rest, because the pancreatic islets are associated with the rest via collagens. For example, the enzyme agent for cell and tissue dissociation of the present disclosure is infused from the pancreatic duct of the isolated pancreas and incubated for a prescribed period. The period time for the incubating may be selected according to conditions of the tissue used, the amount of recombinant collagenase contained in the enzyme agent for cell and tissue dissociation, and the like. Because the pancreatic islets are lighter than the rest tissue in the pancreas, they can be purified after the incubation by a density gradient centrifugation method or the like. It is to be noted that the cell separation method is not limited to the pancreatic islets, and can be suitably used for any of the cell separation for liver, heart, lung, kidney, spleen, adrenal gland, and muscles as well as glandular tissues such as thyroid gland, salivary gland, parotid gland acinus, and mammary tissues; bone tissues such as bones and cartilages; endothelial cells; epithelial cells; adipose tissues and fibroblasts.

EXAMPLES

By way of the examples, the present disclosure will now be specifically described; but the present disclosure is by no means limited by those examples.

Example 1

With a bacmid pCC1BAC-2 (Accession number; NITE BP-00739: Date of deposit: (original deposit); Apr. 28, 2009: Name of depository; Incorporated Administrative Agency National Institute of Technology and Evaluation Patent Microorganisms Depositary (NPMD): Address of depository; 2-5-8, Kazusakamatari, Kisarazu-shi, Chiba 2920818, Japan) containing the gene of the entire coding region of *Grimontia-hollisae*-derived collagenase as a template, amplification was carried out by Expand High Fidelity PCR System (Roche) to add an Nco I site and a Hind III site, respectively, on the 5' side and the 3' side of partial sequence (2040 bp in length) of the collagenase gene, which sequence was induced from the peptide sequence of SEQ ID NO: 5. The following primer set was used for the PCR reaction. In the primer sequence, restriction enzyme sites are underlined.

```
Fwd:
                                     (SEQ ID NO: 6)
AAACCATGGCTTTCGCTGCGGTTGAACAGTGTGATCT

Rvs:
                                     (SEQ ID NO: 7)
AAAAAGCTTTTACTGACGACACTGGTTAC
```

The amplified fragment was treated with Nco I and Hind III; and the resulting DNA fragment was recovered and inserted into a cloning site of a plasmid vector pNY326 to prepare pNY326-Col.74. A *Brevibacillus choshinensis* HPD31-SP3 strain was transformed with this recombinant plasmid to prepare a recombinant.

In addition, a partial sequence (1611 bp in length) of the collagenase gene induced from the peptide sequence of SEQ ID NO: 3 was isolated with the following primer set using a PCR reaction with a bacmid pCC1BAC-2 (NITE BP-00739) containing a gene of the entire coding region of a *Grimontia-hollisae*-derived collagenase as a template. In the primer sequence, sequences homologous to the sequence of both termini of the linear vector are underlined.
Primers:

```
Fwd:
                                     (SEQ ID NO: 8)
CCCATGGCTTTCGCTGCGGTTGAACAGTGTGATCT

Rvs:
                                     (SEQ ID NO: 9)
CATCCTGTTAAGCTTACTGTCGCCCTTCGCCAGC
```

In addition, a linear expression vector pNY326 was prepared by using a PCR reaction with the below primer set. In the primer sequence, sequences homologous to the sequence of both termini of the DNA fragment to be inserted are underlined.
Primers:

```
Fwd:
                                     (SEQ ID NO: 10)
AAGCTTAACAGGATGCGGGG
```

-continued

```
Rvs:
                                      (SEQ ID NO: 11)
AGCGAAAGCCATGGGAGCAA
```

The DNA fragment (1611 bp) encoding the recombinant 60 kDa collagenase of SEQ ID NO: 3 was mixed with the linear expression vector pNY326 at a molar ratio of 2:1; and the mixture was introduced into competent cells by New Tris-PEG method and at the same time transformed into a *Brevibacillus choshinensis* HPD31-SP3 strain, thereby preparing a plasmid pNY326-Col.60 and a recombinant.

Similarly, a partial sequence (1677 bp in length) of the collagenase gene that is induced from the above peptide sequence of SEQ ID NO: 4 was isolated by using a PCR reaction using the following primer set. In the primer sequence, sequences homologous to the sequence of both termini of the linear vector are underlined.
Primers:

```
Fwd:
                                      (SEQ ID NO: 12)
CCCATGGCTTTCGCTGCGGTTGAACAGTGTGATCT

Rvs:
                                      (SEQ ID NO: 13)
CATCCTGTTAAGCTTAGGTATTACCACCAGATTCA
```

Subsequently, the linear expression vector pNY326 was prepared in the same manner as described above; and a plasmid pNY326-Col.62 and a recombinant that contained a DNA fragment (1677 bp) encoding the recombinant 62 kDa collagenase of SEQ ID NO: 4 were prepared. From the above, three kinds of *Brevibacillus choshinensis* recombinants were prepared.

Each of three kinds of the *Brevibacillus choshinensis* recombinants was cultured in 100 ml of 2SYN medium (20 g/L glucose, 40 g/L Bacto Soytone, 5 g/L Bacto Yeast Extract, 0.15 g/L $CaCl_2.2H_2O$, 50 µg/mL neomycin) at 30° C. for 48 hours. A culture medium containing a product of the *Grimontia-hollisae*-derived collagenase gene was centrifuged; and the obtained supernatant was subjected to filter sterilization with a 0.2 µm filter. Subsequently, the supernatant was purified and fractionated by an HPLC system. The HPLC system was performed by anion exchange column chromatography using DEAE-Sepharose. Each culture supernatant was subjected to the column to allow the collagenase to be adsorbed; and thereafter the collagenase was separated and eluted by flowing a 50 mM Bis-Tris HCl buffer (pH 7) while the concentration of NaCl was continuously increased from 0.2 to 1 M. Elutant liquid was, in the order eluted, collected and fractionated into 4-ml aliquots. Subsequently, elutants with 30 kDa or below in size were removed by ultrafiltration and the resultant was dialyzed with a 50 mM Tris HCl buffer containing 0.2 M NaCl and 5 mM $CaCl_2$ at 4° C. to obtain purified 74 kDa collagenase, recombinant 62 kDa collagenase, and recombinant 60 kDa collagenase.

Figure 2:
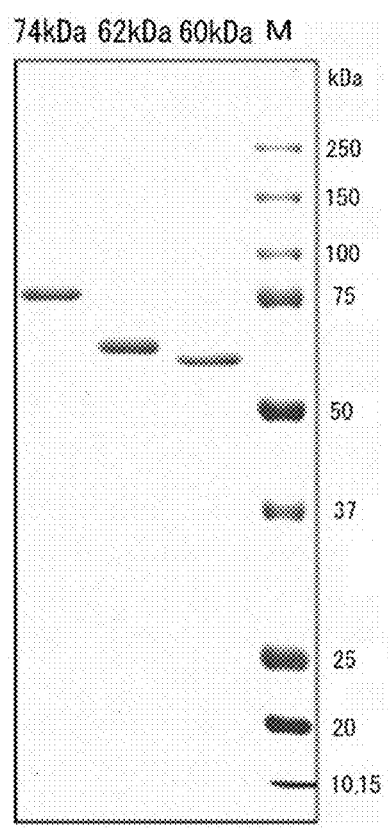
FIG. 2 is a figure showing the result of Example 1 and a figure showing the result of SDS-poly acrylamide gel electrophoresis of the purified enzyme; 74 kDa denotes the 74 kDa collagenase; 62 kDa denotes the recombinant 62 kDa collagenase; 60 kDa denotes the recombinant 60 kDa collagenase; and M denotes a marker.

FIG. 2 shows a figure from SDS-poly acrylamide gel electrophoresis for the purified enzymes. 74 kDa denotes the 74 kDa collagenase, 62 kDa denotes the recombinant 62 kDa collagenase, and 60 kDa denotes the recombinant 60 kDa collagenase.

Example 2

Figure 3:
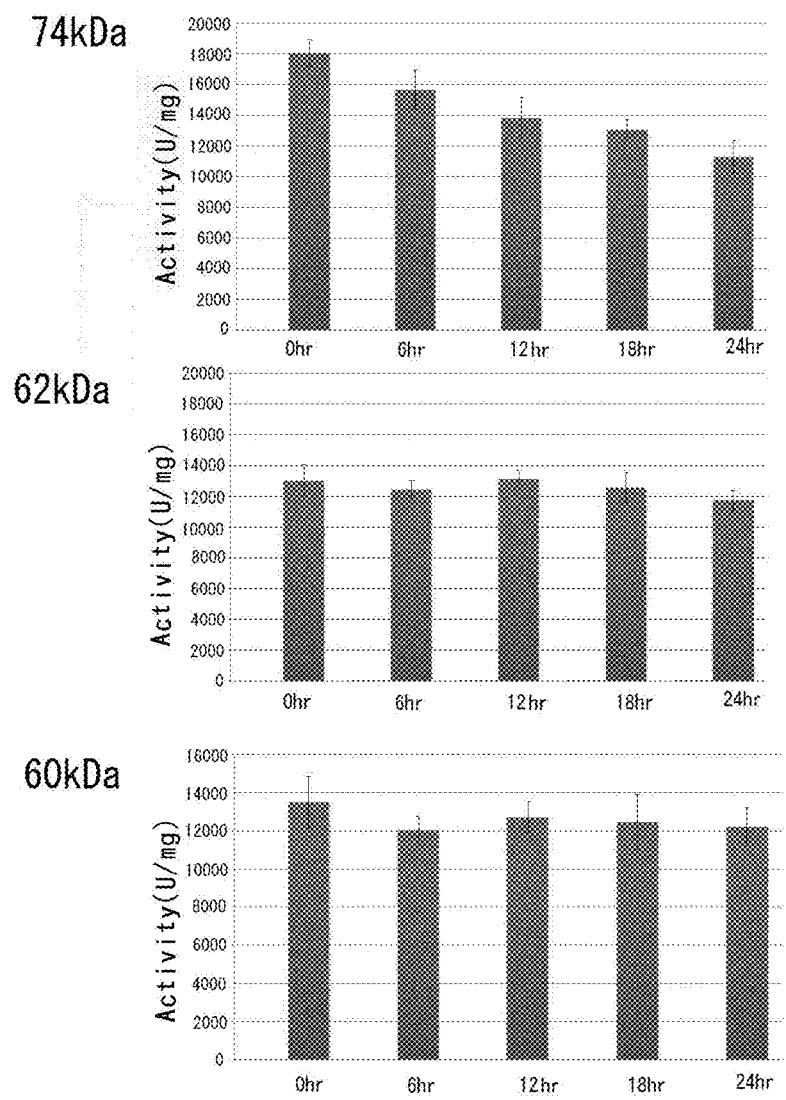
FIG. 3 is a figure showing the result of measuring a change with time in the specific activity from immediately after the 74 kDa collagenase, the recombinant 62 kDa collagenase, and the recombinant 60 kDa collagenase were purified in Example 2.

A change with time in the specific activity of the 74 kDa collagenase, the recombinant 62 kDa collagenase, and the recombinant 60 kDa collagenase obtained in Example 1 was measured by a method described below. The measurement results are shown in FIG. 3. Although 74 kDa had an activity of 18,000 (U/mg) immediately after the purification, the activity was reduced to 11,500 (U/mg) 24 hours after the purification and deceased with time. By contrast, both of the recombinant 62 kDa collagenase and the recombinant 60 kDa collagenase kept an activity of 12,000 (U/mg) from immediately after the purification to the 24 hours passed and had a stable collagenase activity.

Measurement of the specific activity of collagenase: 0.5 µg of collagenase was mixed in 50 mM Tris HCl (pH 7.5) that contained 0.05% fluorescently labeled type I collagen (FITC-collagen), 5 mM $CaCl_2$, and 200 mM NaCl and heated to 30° C. After 30 minutes, EDTA was added to the mixture to stop the enzymatic reaction. To the reaction solution, 50 mM Tris HCl (pH 9.5) containing an equal amount of 70% ethanol was added to extract breakdown products; and the fluorescence intensity was measured by a fluorescence spectrophotometer. In the figure, 1 unit (U) refers to an activity at which 1 µg of collagen is broken down at 30° C. for 1 minute.

Example 3

Figure 4:
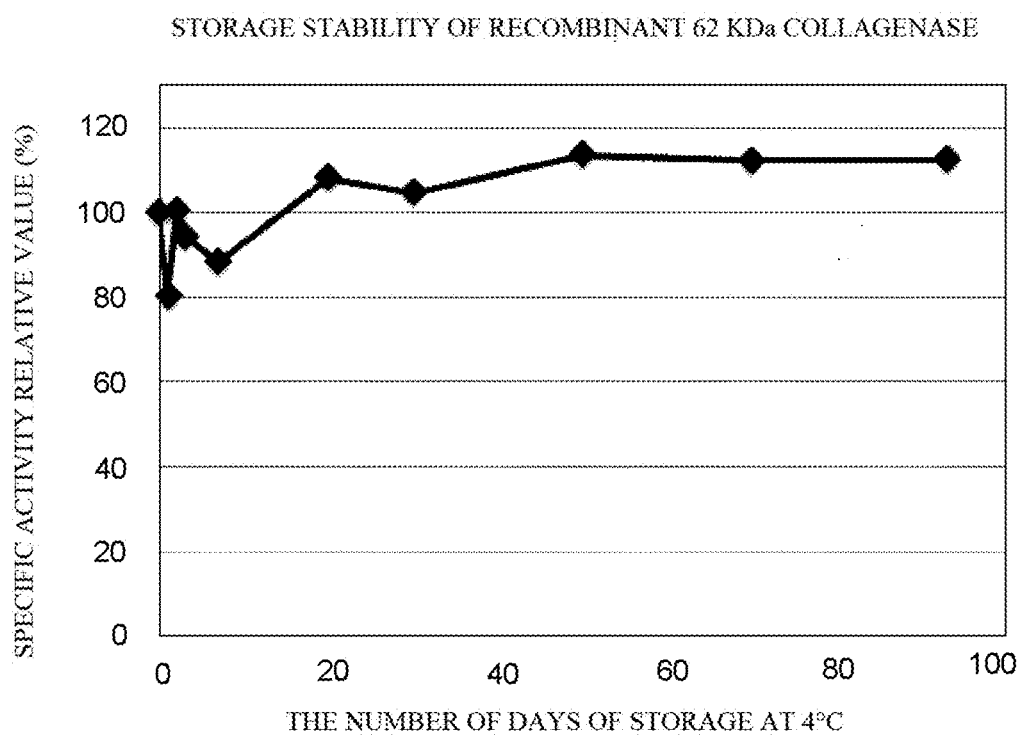
FIG. 4 is a figure showing a change with time in the specific activity when the recombinant 62 kDa collagenase was stored at a temperature of 4° C. in Example 3.

The recombinant 62 kDa collagenase obtained in Example 1 was stored at a temperature of 4° C. and a change with time in the specific activity was evaluated. FIG. 4 shows a relative value with the specific activity value on Day 0 being 100%. As shown in FIG. 4, the high specific activity was able to be stably maintained over 100 days. Note that the recombinant 60 kDa collagenase exhibited the same stability.

Example 4

Figure 5:
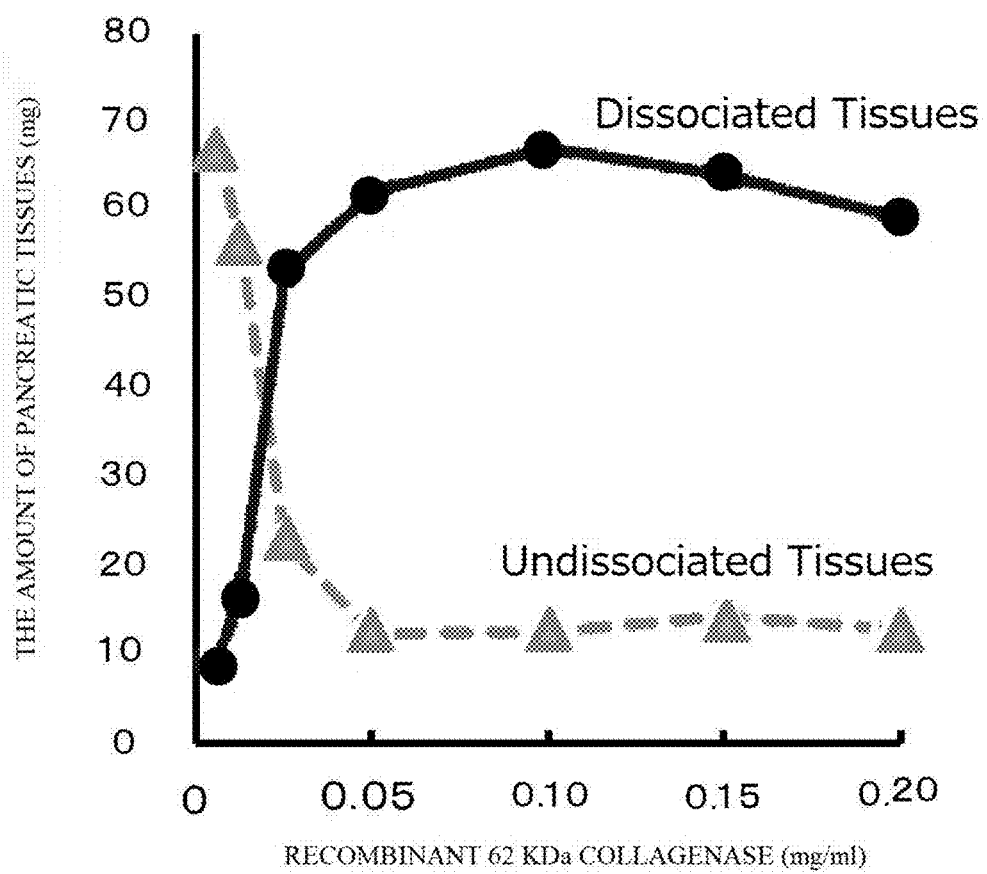
FIG. 5 is a figure showing the result of Example 4 and a figure showing a change in the concentration of the recombinant 62 kDa collagenase contained in the enzyme liquid, the amount of dissociated tissues, and the amount of undissociated tissues.

An ability evaluation to dissociate murine pancreas was carried out with the recombinant 62 kDa collagenase obtained in Example 1. The pancreas was isolated from a mouse, infused with an enzyme liquid containing 0.00625 to 0.20 mg of the recombinant 62 kDa collagenase in 1 ml of HBSS buffer and 0.012 mg of thermolysin (manufactured by Roche Applied Science, a product bundled with trade name "Liberase C/T") via a pancreatic duct, and incubated at 37° C. for 15 minutes. Thereafter, the amount of proteins in fractions (dissociated tissues) that passed through a mesh with an opening of 1 mm and fractions (undissociated tissues) that left on the mesh was measured. Depending on the concentration of the recombinant 62 kDa collagenase contained in the enzyme liquid, the amount of the dissociated tissue increased and, in associated with that, the amount of the undissociated tissue decreased. The results were shown in FIG. 5. As shown in FIG. 5, the reaction reached a plateau at a concentration of the recombinant 62 kDa collagenase of 0.05 mg/ml.

Example 5

Figure 6:
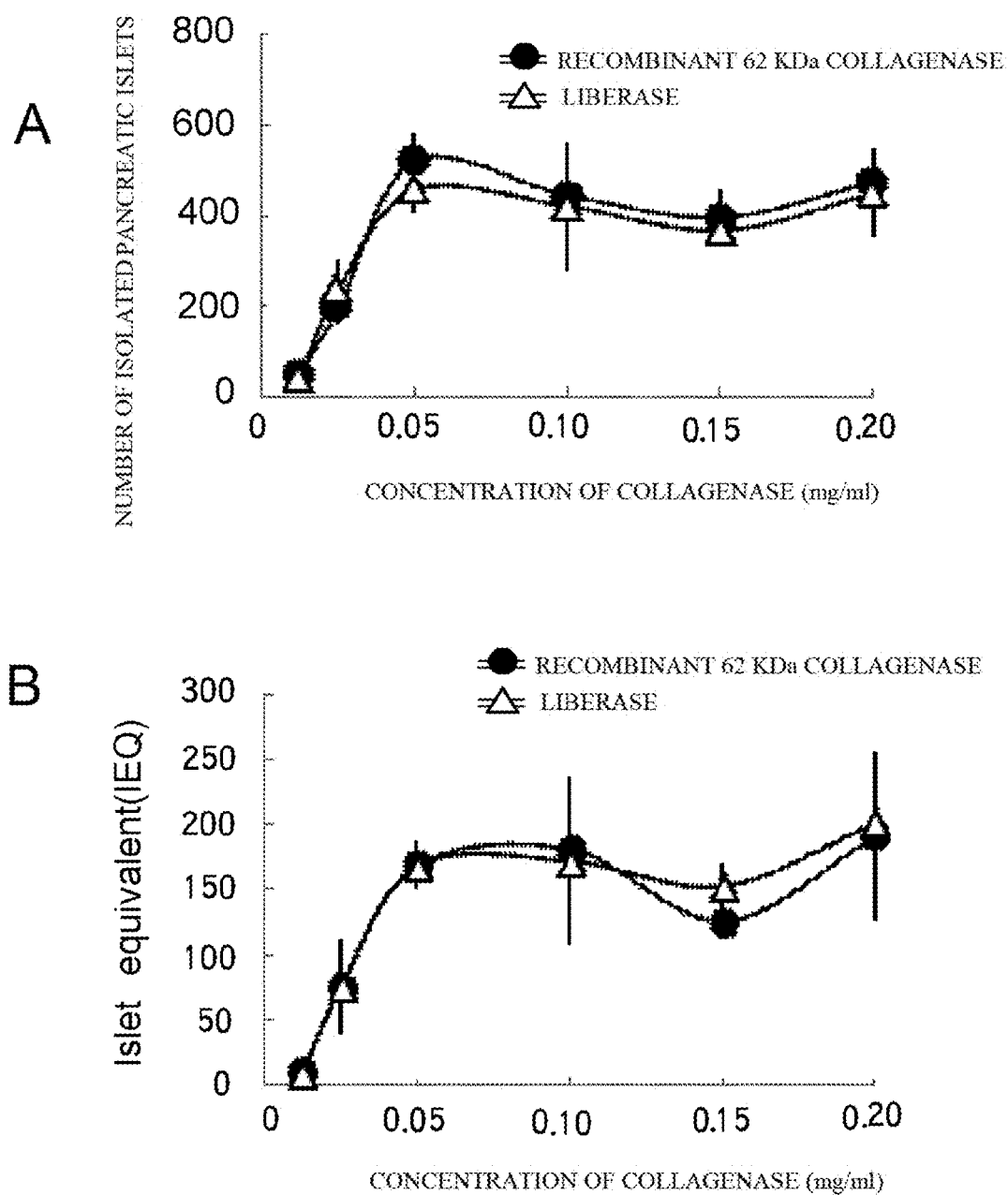
FIG. 6 is a figure showing the results of Example 5 and Comparative Example 1 and a figure showing the results for the number and IEQ of the pancreatic islets that were obtained by carrying out a pancreatic digestion experiment using the recombinant 62 kDa collagenase or a collagenase derived from *Clostridium histolyticum* (liberase)
Figure 7:
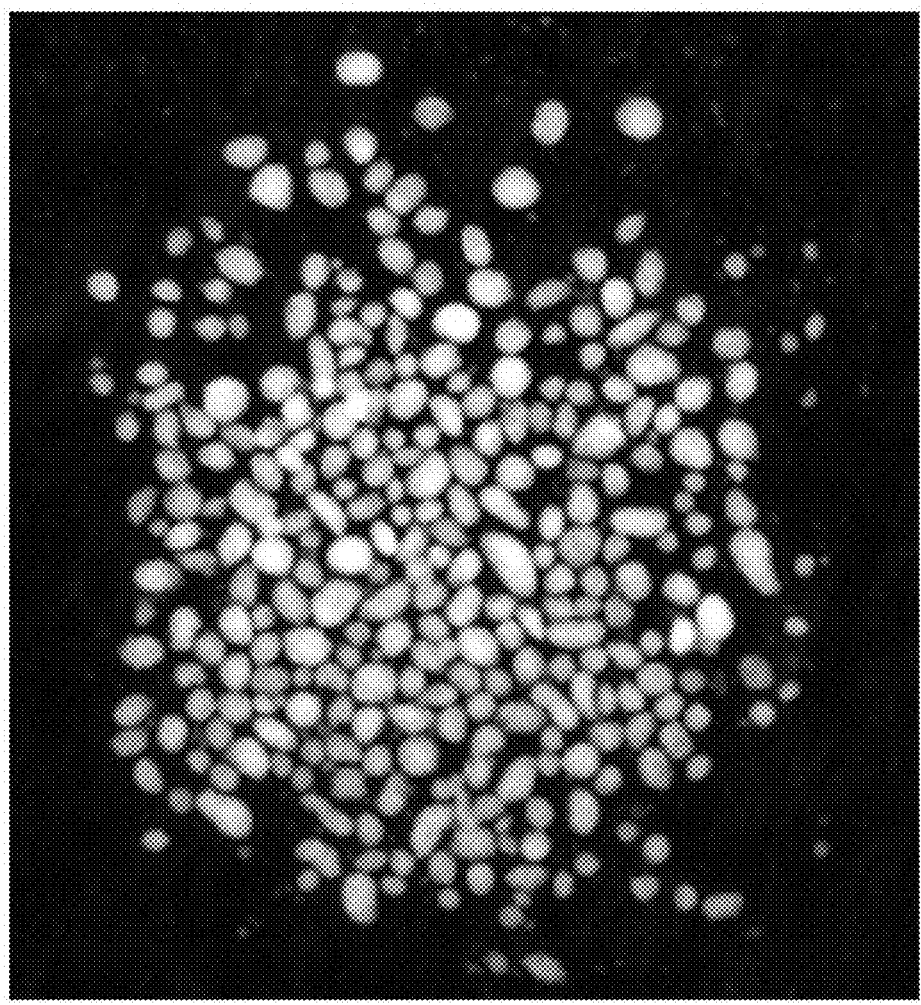
FIG. 7 is a figure showing a photograph of the pancreatic islets under an optical microscope, which pancreatic islets were isolated using the recombinant 62 kDa collagenase in Example 5.

The ability evaluation to isolate functional islets was carried out with the recombinant 62 kDa collagenase obtained in Example 1 in the same manner as described in Example 4, the number of the obtained pancreatic islets was measured and IEQ (Islet Equivalent: an international unit that represents the volume of the pancreatic islets with the pancreatic islets having a diameter of 150 µm being defined as 1) was evaluated. FIG. 6A shows the result for the number of the pancreatic islets at different concentrations of the recombinant 62 kDa collagenase and FIG. 6B shows the result for IEQ. In addition, FIG. 7 shows a photograph of the isolated pancreatic islets under an optical microscope.

Comparative Example 1

The same procedures as described in Example 5 were carried out except that a collagenase derived from *Clostridium histolyticum* (manufactured by Roche Applied Science, trade name "Liberase C/T") was used instead of the recombinant 62 kDa collagenase obtained in Example 1, and the number and IEQ of the pancreatic islets were evaluated. The results are shown in FIG. 6A and FIG. 6B. The recombinant 62 kDa collagenase obtained in Example 1 was able to separate the pancreatic islets from the pancreatic tissue in the same manner as the commercially available conventional product.

Example 6

The pancreatic islets obtained in Example 5 were transplanted under the renal capsule of an STZ-induced diabetic mouse and the blood glucose level was measured with time. While a control group in which the pancreatic islets were not transplanted (n=3: STZ-1, STZ-2, and STZ-3) exhibited a high blood glucose level, the blood glucose level in the pancreatic islet transplantation group (n=5: STZ/islet-1 to STZ/islet-5) decreased to a normal level immediately after the transplant. When the kidney that had been transplanted with the pancreatic islets was removed 39 days after the transplantation, the blood glucose level again increased. The result is shown in FIG. 8A. A photograph of the extracted kidney with the pancreatic islets being transplanted and a photograph of a magnified image of part of the extracted kidney are shown in the upper and lower rows at the far left in FIG. 8B. In addition, the extracted kidney with the pancreatic islets being transplanted was subjected to hematoxylin and eosin staining (H&E staining) and the pancreatic islets were confirmed under the renal capsule; and the pancreatic islets were also stained with an anti-insulin antibody (FIG. 8B). This demonstrates that the pancreatic islets that retain pancreatic islet functions was able to be isolated by the recombinant 62 kDa collagenase obtained in Example 1.

Example 7

Figure 9:
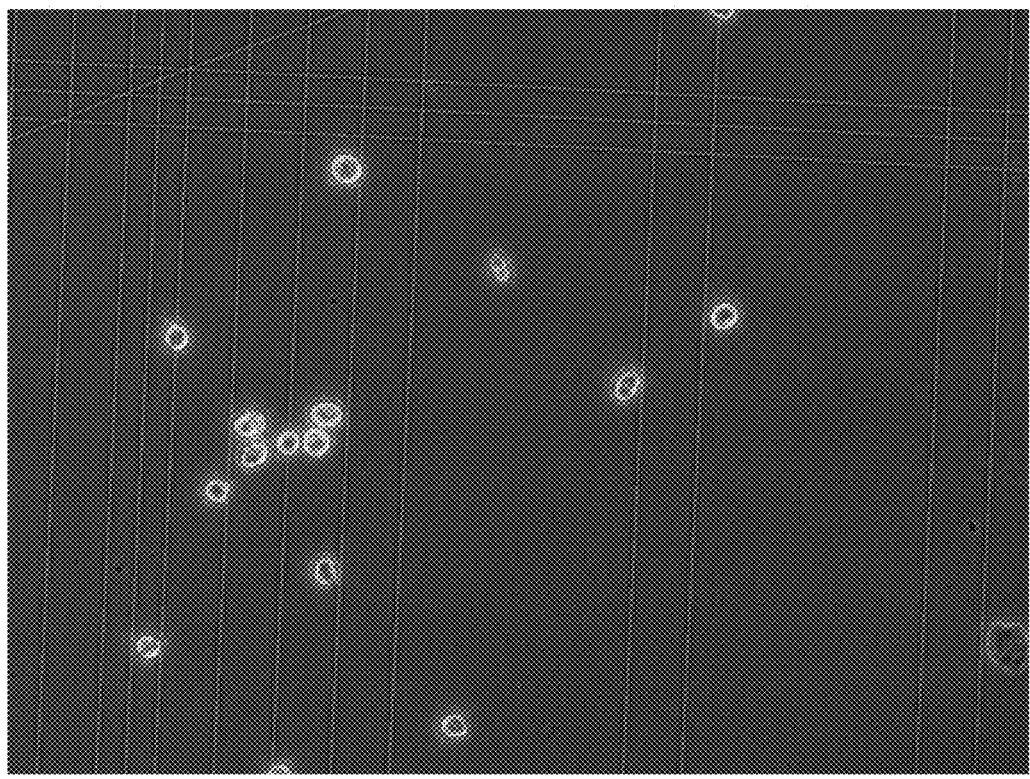
FIG. 9 is a figure showing a photograph image of liver cells separated in Example 7 under a phase-contrast microscope.

An ability evaluation to isolate liver cells was carried out with the recombinant 62 kDa collagenase obtained in Example 1. The blood was removed from the liver of an anesthetized rat under perfusion with HBSS buffer to remove calcium; and then the recombinant 62 kDa collagenase at 0.05 mg/ml and thermolysin at 0.01 mg/ml were perfused into the liver over 10 minutes to add calcium and subsequently the liver was removed. The extracted liver was cooled with ice, cut into fine strips with a scalpel, and filtered with gauze and a strainer. After dead cells were removed, liver cells were centrifuged and recovered. FIG. 9 shows a photograph of the liver cells under a phase-contrast microscope. These liver cells were cultured for seven days and the viability was 98%.

Example 8

The ability of the recombinant 62 kDa collagenase obtained in Example 1 to bind to collagen fibers and the activity of collagenase left in the collagen fibers after washing were evaluated.

To a spin column with a built-in filter, 5 mg of pig skin collagen fibers and a Tris HCl buffer (pH 7.5) containing 400 µl of 0.2 M NaCl and 5 mM $CaCl_2$ were placed; and centrifuged it for two-minute at 10,000 rpm to wash the collagen fiber with the above buffer, such centrifugation was carried out five times in total.

The washing liquid was discarded and 100 µl of enzyme mixture liquid (a Tris HCl buffer (pH 7.5) containing the recombinant 62 kDa collagenase at 0.2 mg/ml, ovalbumin at 0.2 mg/ml, ortho-phenanthroline at 4 mM, NaCl at 0.2 M, and $CaCl_2$ at 5 mM) was added to the collagen fiber on the filter of the spin column and left to stand at 4° C. for 30 min to allow the collagen fiber to bind to the recombinant 62 kDa collagenase.

Figure 10:
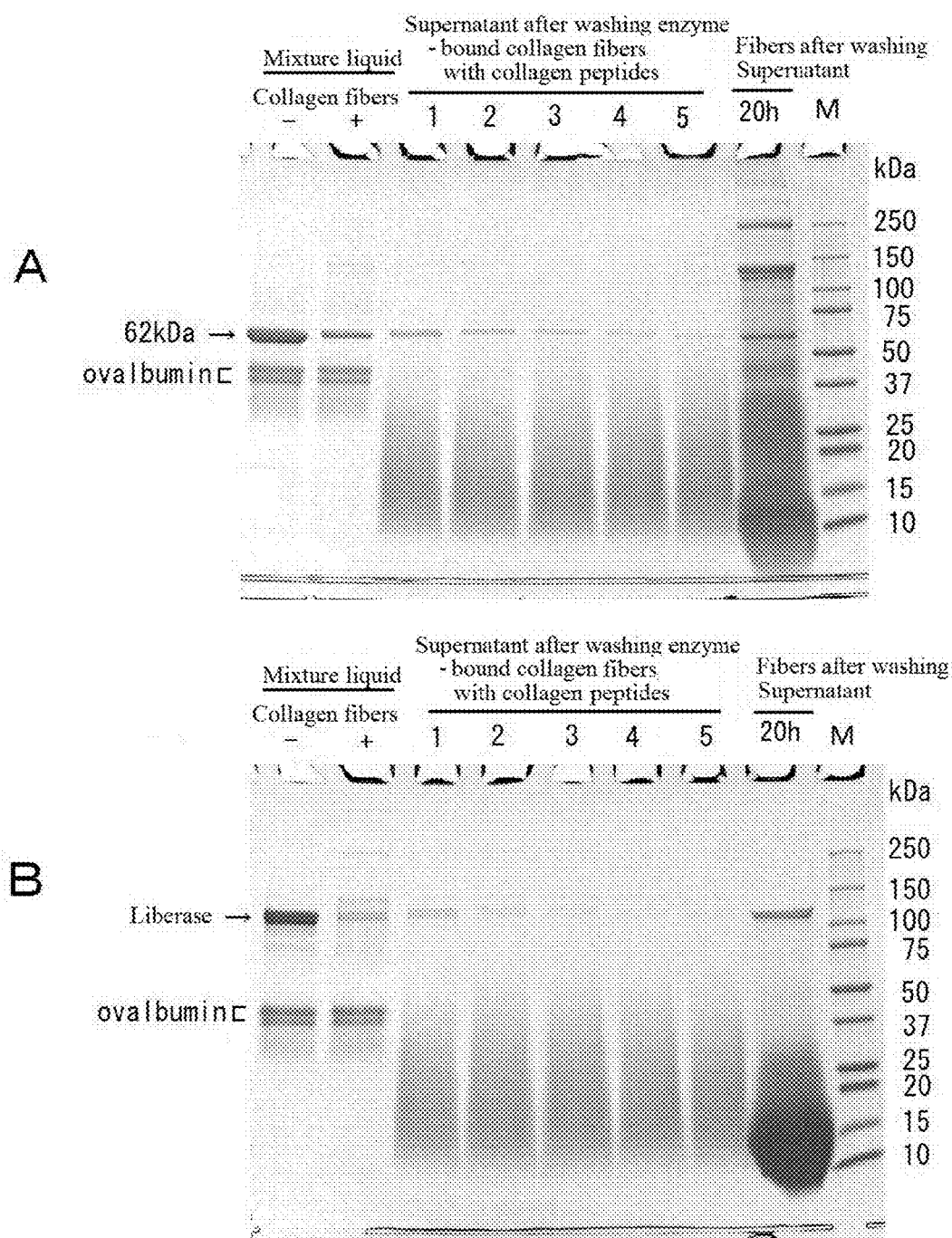

Subsequently, centrifugation was carried out at 10,000 rpm for two minutes to separate the collagen fiber on the above filter from a mixture liquid that passed through the filter. Part of this mixture liquid was analyzed by SDS-PAGE. Note that, for the sake of comparison, the same treatment as described above except that no pig skin collagen fibers were added was carried out and the thus obtained mixture was analyzed by SDS-PAGE as well. The result was shown in FIG. 10A by using "Mixture liquid/collagen fibers '−' or '+'". The band of recombinant 62 kDa collagenase exhibited a weaker band for '+' and a stronger band for '−'. It has been demonstrated that the recombinant 62 kDa collagenase binds to the collagen fiber when mixed with the collagen fiber. It is to be noted that M denotes a marker in FIG. 10.

Subsequently, the collagenase-bound collagen fiber in the spin column was collected to a 2 ml tube and added with a Tris HCl buffer (pH 7.5) containing 0.2 M NaCl, 5 mM $CaCl_2$, 0.1 mg/ml collagen peptide, and 4 mM ortho-phenanthroline. The mixture was left to stand at 4° C. for 10 minutes and centrifuged at 10,000 rpm for two minutes; and the precipitate was washed with a buffer containing the above collagen peptide. The centrifugation was carried out five times in total. The supernatant from each of five washings was analyzed by SDS-PAGE. The result was shown in FIG. 10A by using "Supernatant after washing enzyme-bound collagen fiber with collagen peptide/1, 2, 3, 4, and 5". The number indicates how many times the supernatant was washed. The recombinant 62 kDa collagenase exhibited a weak band in every case from the first to the fifth washing, which demonstrated that the recombinant 62 kDa collagenase bound to the collagen fiber remained in the collagen fiber even when washed with the collagen peptide.

Figure 11:
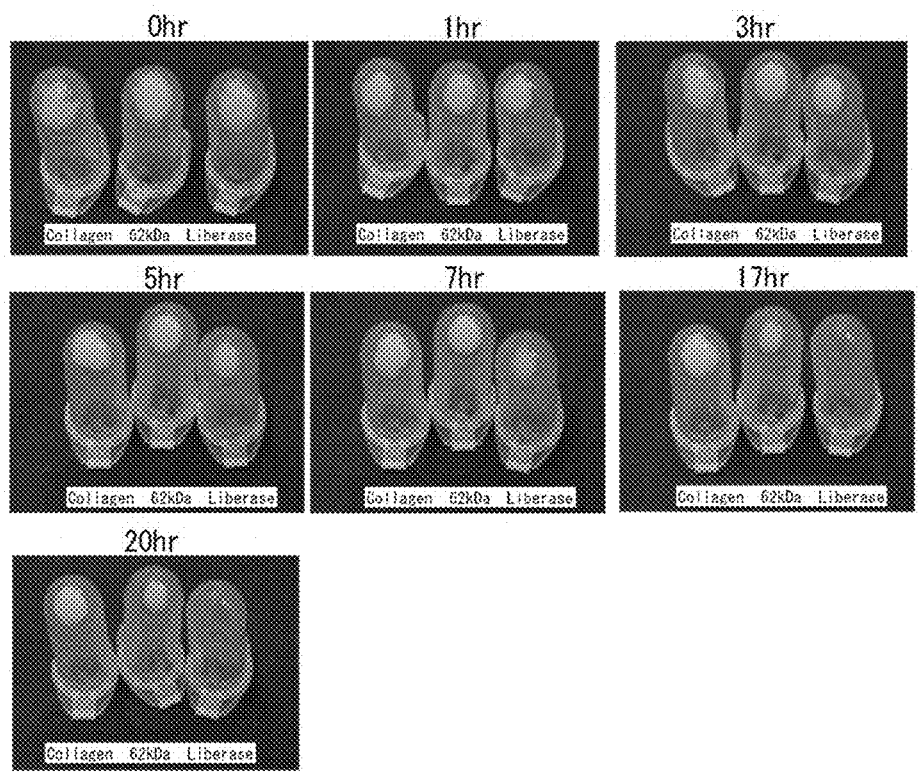
FIG. 11 is a figure showing the results of Example 8 and Comparative Example 2 and a figure showing the washed collagen fiber was broken down with time by the remaining collagenase.

Further, 500 µl of Tris HCl buffer containing 0.2 M NaCl, 5 mM $CaCl_2$, 2 µg/ml $ZnSO_4.7H_2O$ was added to the collagenase-bound collagen fiber obtained by centrifugation and the resulting mixture was left to stand at 37° C. Observation was visually made at the beginning of the standing, and 1 hour, 3 hours, 5 hours, 7 hours, 17 hours, and 20 hours after the standing. FIG. 11 shows a change with time in the collagen fiber collected on the bottom of a 2 ml tube. Further, the supernatant left to stand for 20 hours was analyzed by SDS-PAGE. The result of SDS-PAGE is shown in FIG. 10A by using "Supernatant of fiber after washing/20 h". The supernatant obtained 20 hours after the standing exhibited a strong band for the collagen breakdown product; and it has thus demonstrated that the collagen fiber-bound collagenase remains in the collagen fiber even after washed and produces the collagenase activity. It is to be noted that, in "Supernatant of fiber after washing/20 h", a strong 62 kDa band appeared in conjunction with the band of the collagen breakdown product; and it has thus demonstrated that the collagenase promptly separates after the breakdown of the collagen.

Comparative Example 2

The same procedures as described in Example 8 were carried out except that an equal amount of a collagenase derived from *Clostridium* (manufactured by Roche Applied Science, trade name "Liberase C/T") was used instead of the recombinant 62 kDa collagenase. The results are shown in FIG. 10B and FIG. 11.

As shown in FIG. 10B, the same tendencies as seen in the recombinant 62 kDa collagenase were exhibited in that a weak band of the liberase was seen in the '+' column with the collagen fiber and thus the liberase was associated with the collagen fiber; and that the washing supernatant obtained when the collagenase-bound collagen fiber was washed with the collagen peptide exhibited a weak band of the liberase throughout the washings 1 to 5 and thus the collagenase remained in the collagen fiber even when washed with the collagen peptide; and the like.

On the other hand, a difference in the enzymatic activity of the collagenase left in the collagen fiber was observed between the recombinant 62 kDa collagenase and the liberase, as shown in FIG. 11. In FIG. 11, the higher collagenase activity the remaining enzyme has, the more rapidly the amount of the collagen fiber decreases. The recombinant 62 kDa collagenase exhibits the decrease in the amount of the collagen fiber to a lesser extent than the liberase. Because the remaining enzyme causes cell damage in a treatment such as pancreatic islet separation, it is preferred that, after the pancreatic islet isolation, no enzymes be left or that the collagenase activity be reduced even when the remaining enzyme is present. As shown in FIG. 10A and FIG. 10B, the recombinant 62 kDa collagenase and the liberase bind to the collagen fiber and partially remain in the collagen fiber even when washed with a collagen peptide five times. Yet, there was a difference in the activity of the remaining enzyme between both enzymes; and the collagenase activity of the recombinant 62 kDa collagenase decreased more than that of the liberase. Although details are unknown, that is seemingly because the recombinant 62 kDa collagenase, unlike the liberase, does not have "CBD" which is capable of binding to the collagen fiber. The linkage with collagen fiber may be weak due to the absence of "CBD", resulting in the difference in the collagenase activity by the remaining enzyme.

Example 9

The recombinant 62 kDa collagenase obtained in Example 1 and a collagenase derived from *Clostridium histolyticum* (manufactured by Roche Applied Science, trade name "Liberase C/T") were evaluated for the activity of digesting a fluorescently labeled type I collagen (hereinafter, referred to as FITC-collagen) and a synthetic substrate N-(3[2-furyl]acryloyl)-Leu-Gly-Pro-Ala (hereinafter, referred to as FALGPA).

A 50 mM Tris-HCl (pH 7.5, 30° C.) buffer containing 0.2 M NaCl and 5 mM $CaCl_2$ was used for the FITC-collagen and a 50 mM tricine (pH 7.5, 30° C.) containing 0.4 M NaCl and 40 mM $CaCl_2$ was for FALGPA. When the FITC-collagen was used as a substrate, 0.5 µg of the above collagenases was added; and when FALGPA was used as a substrate, 1.0 µg of the recombinant 62 kDa collagenase or 2.5 µg of Liberase C/T was added. FALGPA was detected and quantified by a microplate reader to evaluate the activity of breaking down FALGPA. An activity by which 1 mg of enzyme digested 1 µmole of the above peptide in 1 ml of a reaction system for 1 minute was calculated as a specific activity of 1 U/mg. The obtained specific activity is shown in Table 1. Not only is the recombinant 62 kDa collagenase capable of digesting the collagen but also has an excellent activity of digesting the synthetic substrate FALGPA; and it has therefore been implied that the collagenase has an excellent property of digesting gelatin as well as collagen.

TABLE 1

| | | Parameters of collagenase activity | | | |
|---|---|---|---|---|---|
| Substrate | Collagenase | Specific activity (U/mg) | Michaelis constant (mM) | Maximum rate (mM/s) | Molecular activity ($s^{-1}$) |
| FITC-collagen | Recombinant 62 kDa | 5,490 | $(1.1 \pm 0.35) \times 10^{-3}$ | $(4.1 \pm 0.84) \times 10^{-4}$ | 25.1 ± 5.2 |
| | Liberase C/T | 1,766 | $(1.9 \pm 0.42) \times 10^{-3}$ | $(1.6 \pm 0.39) \times 10^{-4}$ | 18.7 ± 4.5 |
| FALGPA | Recombinant 62 kDa | 9.39 | 2.28 ± 0.23 | 0.6 ± 0.13 | 37.5 ± 8.0 |
| | Liberase C/T | 2.60 | 2.03 ± 0.48 | 0.2 ± 0.03 | 22.2 ± 2.9 |

Example 10

Figure 12:
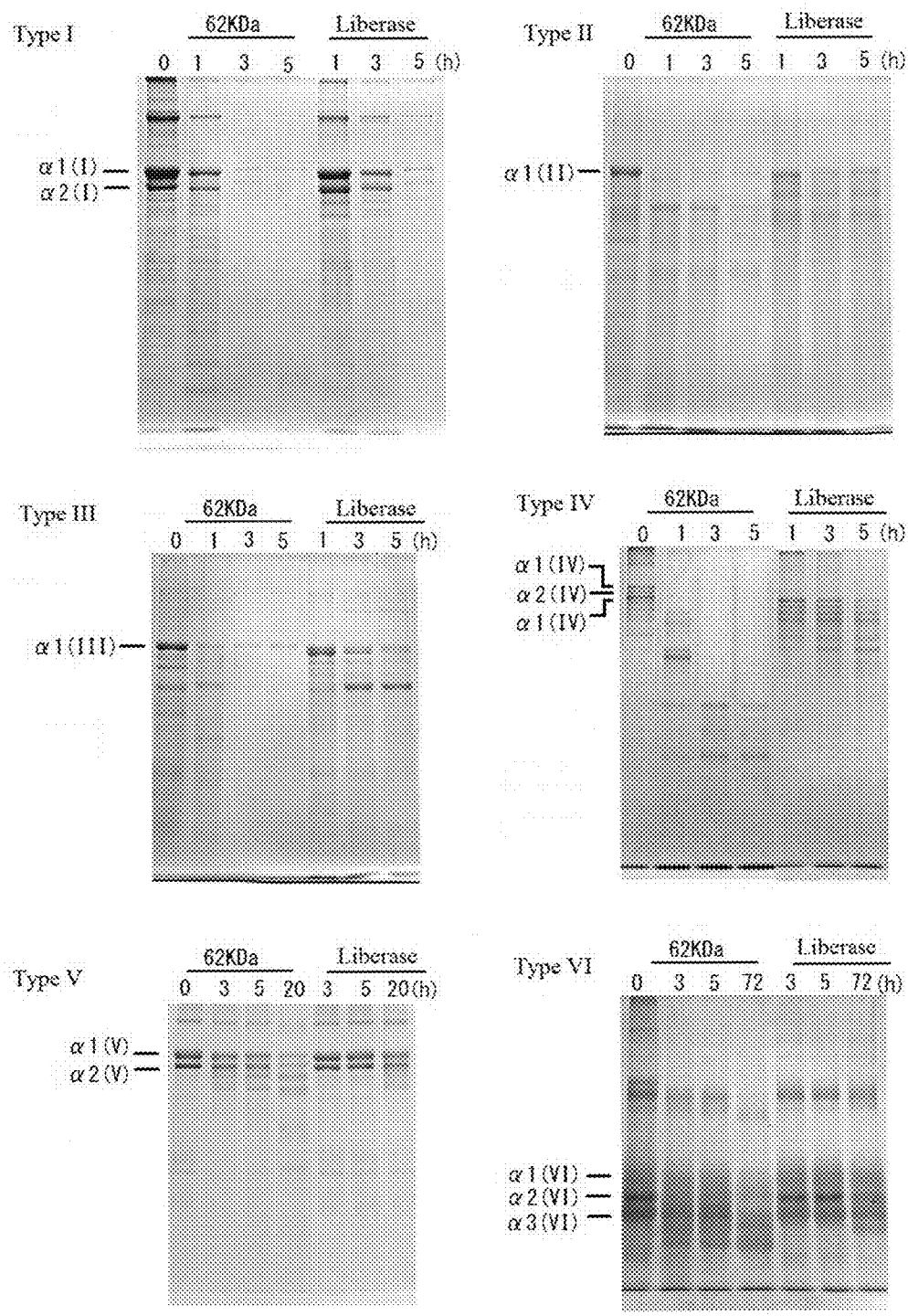
FIG. 12 is a figure showing the result of Example 10 and a figure showing an electrophoresis image after the recombinant 62 kDa collagenase was incubated with type I, type II, type III, type IV, type V, and type VI collagens.

Using the recombinant 62 kDa collagenase obtained in Example 1, the activity to type I, type II, type III, type IV, type V, and type VI collagens were evaluated. To 0.5 mg/ml the above collagen, collagenase dissolved at 1 µg/ml in a 50 mM Tris-HCl buffer (pH 7.5) containing 0.2 M NaCl and 5 mM $CaCl_2$. The mixture was incubated at 30° C. and sampled at the beginning of incubation and 1 hour, 3 hours, and 5 hours after the incubation; and the sample was analyzed by electrophoresis. For the sake of comparison, the same procedures as described above were carried out using a collagenase derived from *Clostridium histolyticum* (manufactured by Roche Applied Science, trade name "Liberase C/T") instead. The result is shown in FIG. 12. It is to be noted that, in FIG. 12, "62 kDa" denotes the column using the recombinant 62 kDa collagenase and "liberase" denotes the column using the collagenase derived from *Clostridium histolyticum*.

With regard to the type I collagen, judging from the extent of disappearance of the bands of α1(I) and α2(I) 3 hours and 5 hours after the incubation, the recombinant 62 kDa collagenase seems to more rapidly digest the type I collagen than liberase. This tendency was also similarly observed for the type II, type III, type IV, type V, and type VI collagens. In particular, with regard to the type IV and type V collagens, the band become weaker when the recombinant 62 kDa collagenase is used to react for three hours or five hours whereas the bands do not disappear when the liberase is used. With regard to the type VI collagen, the band become weaker when the recombinant 62 kDa collagenase is used to react for 72 hours whereas the band does not disappear when the liberase is used. It has been implied that the recombinant 62 kDa collagenase is possibly capable of digesting the collagens that are not readily digested by the liberase.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

The present disclosure is based on Japanese Patent Application No. 2014-044205 filed in Mar. 6, 2014. The specification, claims, and drawings of Japanese Patent Application No. 2014-044205 are incorporated in the present specification by reference in their entirety.

INDUSTRIAL APPLICABILITY

According to the present disclosure, recombinant collagenases with a stable specific activity and enzyme agents for cell and tissue dissociation that contains such a recombinant collagenase are provide and useful.

Accession Numbers
NITE BP-00739

The invention claimed is:

1. A recombinant collagenase that is genetically derived from *Grimontia hollisae* collagenase (SEQ ID No: 1) which comprises, from N terminal to C-terminal, a collagenase catalytic domain, a linker region sequence, and a prepeptidase C-terminal domain,
   which recombinant collagenase comprises at least the collagenase catalytic domain but does not comprise at least the prepeptidase C-terminal domain of *Grimontia hollisae* collagenase;
   wherein the recombinant collagenase has the amino acid sequence represented in SEQ ID No: 3, SEQ ID No: 4, SEQ ID No: 14, or SEQ ID No:15.

2. An enzyme agent for cell and tissue dissociation comprising the recombinant collagenase according to claim 1.

3. The enzyme agent for cell and tissue dissociation according to claim 2 that is used for separation of one or more cells selected from the group consisting of: pancreatic islets, a liver, a heart, lungs, kidneys, a spleen, adrenal glands, muscles, thyroid glands, salivary glands, parotid gland acini, mammary tissues, bones, cartilages, endothelial cells, epithelial cells, adipose tissues and fibroblasts.

4. An enzyme agent for digestion of collagen IV, collagen V, or collagen VI comprising the recombinant collagenase according to claim 1.

* * * * *